US012685730B2

(12) United States Patent
Saito et al.

(10) Patent No.: US 12,685,730 B2
(45) Date of Patent: Jul. 21, 2026

(54) PHARMACEUTICAL COMPOSITION FOR KERATOSIS AND USE THEREOF

(71) Applicant: TANABE PHARMA CORPORATION, Osaka (JP)

(72) Inventors: Ryuta Saito, Osaka (JP); Yasuaki Matsushita, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 19/323,422

(22) Filed: Sep. 9, 2025

(65) Prior Publication Data

US 2026/0007657 A1 Jan. 8, 2026

Related U.S. Application Data

(63) Continuation of application No. PCT/JP2025/023148, filed on Jun. 27, 2025.

(30) Foreign Application Priority Data

Jun. 28, 2024 (JP) ................................. 2024-104616

(51) Int. Cl.
*A61K 31/495* (2006.01)
*A61P 17/00* (2006.01)

(52) U.S. Cl.
CPC ............ *A61K 31/495* (2013.01); *A61P 17/00* (2018.01)

(58) Field of Classification Search
CPC .............................. A61K 31/495; A61P 17/00
See application file for complete search history.

(56) References Cited

U.S. PATENT DOCUMENTS

| | | | | |
|---|---|---|---|---|
| 5,053,409 | A | 10/1991 | Okushima et al. | |
| 5,990,113 | A | 11/1999 | Yamazaki et al. | |
| 9,980,983 | B2 * | 5/2018 | Shanler .................... | A61K 8/22 |
| 2010/0130603 | A1 | 5/2010 | Takahashi | |

FOREIGN PATENT DOCUMENTS

| | | | |
|---|---|---|---|
| EP | 0779283 | A1 | 6/1997 |
| JP | H03-7263 | A | 1/1991 |
| JP | H09-221479 | A | 8/1997 |
| JP | 2016-065023 | A | 4/2016 |
| WO | WO 99/40919 | A1 | 8/1999 |
| WO | WO 2004/069275 | A1 | 8/2004 |
| WO | WO 2008/111296 | A1 | 9/2008 |
| WO | WO 2013/125543 | A1 | 8/2013 |
| WO | WO 2017/126488 | A1 | 7/2017 |

OTHER PUBLICATIONS

Ahn et al., (2003) “Multiple Effects of SERCA2b Mutations Associated with Darier’s Disease”, The Journal of Biological Chemistry, 278(23):20795-20801.

Cooper et al., (2003) “Darier’s Disease Epidemiology, Pathophysiology, and Management”, American Journal of Clinical Dermatology, 4(2):97-105.

Fransen et al., (2020) “Contractile Behavior of Mouse Aorta Depends on SERCA2 Isoform Distribution: Effects of Replacing SERCA2a by SERCA2b”, Frontiers in Physiology, vol. 11.

Iwata et al., (2024) “Clinical Practice Guidelines for Familial Benign Chronic Pemphigus 2023”, Journal of the Japanese Dermatological Association, 134(2):273-287.

Kawasumi et al., (2007) “Caldaret, an Intracellular Ca2+ Handling Modulator, Limits Infarct Size of Reperfused Canine Heart”, Journal of Pharmacological Sciences, pp. 222-233.

Prestle et al., (2003) “Ca2+-Handling Proteins and Heart Failure: Novel Molecular Targets?”, Current Medicinal Chemistry, 10(11): 967-981.

Satoh et al., (2003) “Effects of MCC-135 on $Ca^{2+}$ uptake by sarcoplasmic reticulum and myofilament sensitivity to $Ca^{2+}$ in isolated ventricular muscles of rats with diabetic cardiomyopathy”, Molecular and Cellular Biochemistry, vol. 249, pp. 45-51.

British Association of Dermatologists (2020) “Darier Disease”, Patient Information Leaflet, Registered Charity No. 258474.

Bachar-Wikstrom et al. (2020) “Darier disease is associated with heart failure: a cross-sectional case-control and population based study”, Scientific Reports, vol. 10, No. 6886, pp. 1-8.

English Translation of International Search Report issued in International Application No. PCT/JP2025/023148, Aug. 26, 2025 (3 pages).

Ikeda et al. (2005) “Autoimmune Bullous Disease and Hereditary Bullous Disease: Recent Topics—Darier disease and Hailey-Hailey disease”, The Japanese Journal of Dermatology, 115(13):2116-2119.

International Search Report and Written Opinion issued in International Application No. PCT/JP2025/023148, Aug. 26, 2025 (10 pages).

Iwata et al. (2023) “Understanding of Keratosis: Darier disease and Hailey-Hailey disease”, Dermatology, 4(2):193-199.

Prasad et al. (2015) “SERCA2 Haploinsufficiency in a Mouse Model of Darier Disease Causes a Selective Predisposition to Heart Failure”, BioMed Research International, vol. 2015, Article ID 251598, 21 pages.

Sugiyama et al. (2019) “Development of Novel Drug Treatment for Heart Failure with Preserved Ejection Function (HFpEF)”, Okinaka Memorial Institute for Medical Research, No. 45, pp. 98-101.

Takahashi et al. (2008) “Searching for Therapeutic Agents for Darier Disease and Understanding of Pathological Conditions”, Skin Research, 7(2):277.

Office Action issued in corresponding Taiwanese Patent Application No. 114124474 on Jan. 19, 2026 (15 pages).

Satoh et al., (2003) “Effects of MCC-135 on Ca2+ uptake by sarcoplasmic reticulum and myofilament sensitivity to Ca2+ in isolated ventricular muscles of rats with diabetic cardiomyopathy”, Molecular and Cellular Biochemistry, vol. 249, pp. 45-51 (7 pages).

* cited by examiner

*Primary Examiner* — Sahar Javanmard
(74) *Attorney, Agent, or Firm* — Finnegan, Henderson, Farabow, Garrett & Dunner, LLP

(57) ABSTRACT

A pharmaceutical composition for keratosis contains 5-methyl-2-(1-piperazinyl)benzenesulfonic acid. The compound may be in a form of an anhydrate thereof, a salt thereof, a hydrate or solvate thereof, or a hydrate or solvate of a salt thereof, and the hydrate is, for example, 5-methyl-2-(1-piperazinyl)benzenesulfonic acid monohydrate. The keratosis is, for example, Darier’s disease or psoriasis.

20 Claims, 6 Drawing Sheets

| IL-22 (ng/mL) | 0 | 20 | 20 | 20 | 20 | 20 |
|---|---|---|---|---|---|---|
| Compound A (µmol/L) | 0 | 0 | 1 | 3 | 10 | 30 |
| No. | 1-N | 1-C | 1-1 | 1-2 | 1-3 | 1-4 |

| Thapsigargin (nmol/L) | 0 | 30 | 30 | 30 | 30 |
|---|---|---|---|---|---|
| Compound A (μmol/L) | 0 | 0 | 1 | 3 | 10 |
| No. | 2-N | 2-C | 2-1 | 2-2 | 2-3 |

| Thapsigargin (nmol/L) | 0 | 30 | 30 | 30 | 30 |
|---|---|---|---|---|---|
| Compound A (μmol/L) | 0 | 0 | 1 | 3 | 10 |
| No. | 2-N | 2-C | 2-1 | 2-2 | 2-3 |

| | | | | | |
|---|---|---|---|---|---|
| Thapsigargin (nmol/L) | 0 | 30 | 30 | 30 | 30 |
| Compound A (μmol/L) | 0 | 0 | 1 | 3 | 10 |
| No. | 2-N | 2-C | 2-1 | 2-2 | 2-3 |

| | | | |
|---|---|---|---|
| Thapsigargin (nmol/L) | 0 | 30 | 30 |
| Compound A (μmol/L) | 0 | 0 | 10 |
| No. | 2-N | 2-C | 2-3 |

| | | | |
|---|---|---|---|
| Thapsigargin (nmol/L) | 0 | 30 | 30 |
| Compound A (μmol/L) | 0 | 0 | 10 |
| No. | 2-N | 2-C | 2-3 |

| | | | |
|---|---|---|---|
| Thapsigargin (nmol/L) | 0 | 30 | 30 |
| Compound A (μmol/L) | 0 | 0 | 10 |
| No. | 2-N | 2-C | 2-3 |

| | | | |
|---|---|---|---|
| Thapsigargin (nmol/L) | 0 | 30 | 30 |
| Compound A (µmol/L) | 0 | 0 | 10 |
| No. | 2-N | 2-C | 2-3 |

| | | | |
|---|---|---|---|
| Imiquimod 5% cream (62.5 mg per day) | - | + | + |
| Compound A (30 mg/kg, p.o., b.i.d.) | - | - | + |
| No. | 3-N | 3-C | 3-1 |

PHARMACEUTICAL COMPOSITION FOR KERATOSIS AND USE THEREOF

CROSS-REFERENCE TO RELATED APPLICATIONS

The present application is a continuation of and claims the benefit of priority to International Application No. PCT/JP2025/023148, filed Jun. 27, 2025, which is based upon and claims the benefit of priority to Japanese Application No. 2024-104616, filed Jun. 28, 2024. The entire contents of these applications are incorporated herein by reference.

BACKGROUND OF THE INVENTION

Field of the Invention

The present invention relates to a pharmaceutical composition for keratosis and a method for treating or preventing keratosis.

Description of Background Art

Darier's disease is a type of keratosis, a skin disorder, and is a condition in which keratotic papules appear due to hyperkeratosis, acantholysis, and dyskeratosis in the epidermis (Susan M. Cooper and Susan M. Burge, Darier's Disease Epidemiology, Pathophysiology, and Management, Am J Clin Dermatol 2003; 4 (2): 97-105). The entire contents of this publication are incorporated herein by reference.

SUMMARY OF THE INVENTION

According to one aspect of the present invention, a pharmaceutical composition for keratosis includes 5-methyl-2-(1-piperazinyl)benzenesulfonic acid.

According to another aspect of the present invention, a pharmaceutical composition for acantholysis in keratosis includes 5-methyl-2-(1-piperazinyl)benzenesulfonic acid.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
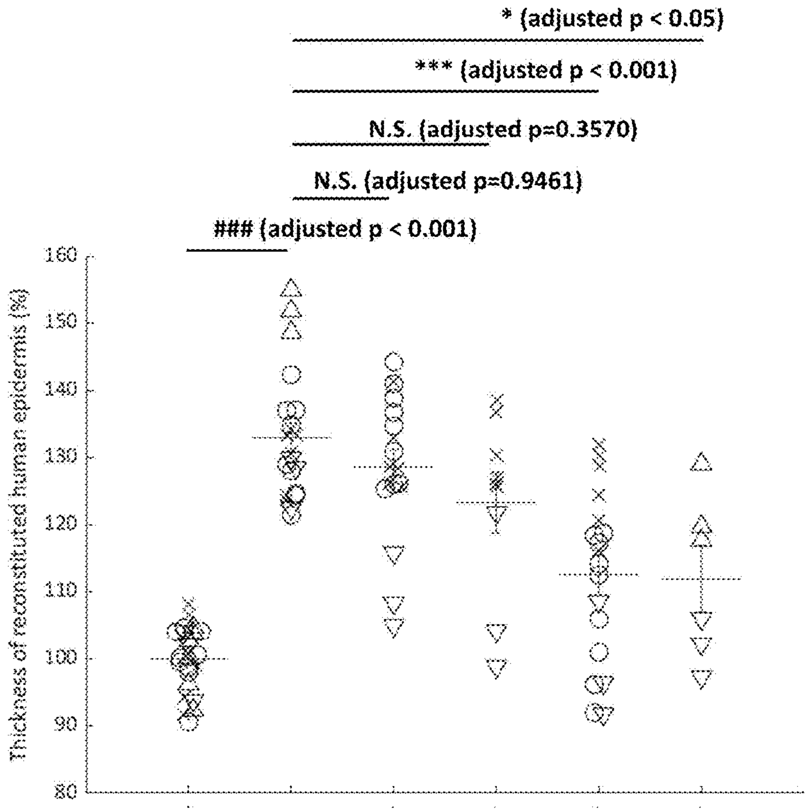
FIG. 1 is a graph showing a relationship between administration of 5-methyl-2-(1-piperazinyl)benzenesulfonic acid monohydrate and epidermal thickness in in vitro epidermal tissue in Example 1.

Embodiments will now be described with reference to the accompanying drawings, wherein like reference numerals designate corresponding or identical elements throughout the various drawings.

In the present specification, the treatment of a disease includes, for example, the meaning of curing the disease, achieving remission of the disease, alleviation of the disease, or suppressing progression of the disease. Further, the treatment of a disease includes, for example, the meaning of treating symptoms caused by the disease (for example, cure, remission, alleviation, or suppression of the symptoms). The prevention of a disease includes, for example, the meaning of preventing the onset of the disease, preventing development of the disease, or preventing recurrence of the disease. Further, the prevention of a disease includes, for example, the meaning of preventing symptoms caused by the disease (for example, preventing occurrence of symptoms or preventing recurrence of symptoms). In the present specification, the treatment or prevention of a disease can also be referred to as, for example, suppression of the disease. Further, the treatment or prevention of symptoms caused by a disease can also be referred to as, for example, suppression of the symptoms caused by the disease.

The composition of the "epidermis" of the skin is typically the stratum corneum, granular layer, spinous layer, and basal layer.

In the present specification, treatment refers to, for example, a procedure administered to a subject diagnosed by a physician as having a disease or symptoms of a disease. Further, in the present specification, prevention refers to, for example, a procedure administered to a subject who has not developed a disease or symptoms of a disease, with the purpose of preventing the onset of the disease or its symptoms. The subject may be, for example, a test subject or participant, and may be a human (patient) or a non-human animal (affected animal). In the present specification, the term “patient” may include, for example, the meaning of an affected non-human animal and may be interpreted as such. Further, when the subject has not developed the disease or its symptoms, the subject may be referred to as a healthy individual (healthy human or healthy non-human animal) with respect to the disease or symptoms of interest.

Hereinafter, the present invention will be described with reference to specific examples. However, the present invention is not limited to these examples. Unless otherwise specified, the embodiments exemplified below can be cross-referenced with one another.

Pharmaceutical Composition for Keratosis

A pharmaceutical composition for keratosis according to an embodiment of the present invention contains 5-methyl-2-(1-piperazinyl)benzenesulfonic acid, and other compositions, conditions, and the like are not particularly limited.

According to the pharmaceutical composition for keratosis described above, treatment or prevention of keratosis can be performed. A pharmaceutical composition for keratosis according to an embodiment of the present invention may be used, for example, for the purpose of treatment, for the purpose of prevention, or for the purpose of both treatment and prevention. Hereinafter, in the present specification, the term “treatment/prevention” can be interpreted as meaning treatment, prevention, or both treatment and prevention. According to a pharmaceutical composition for keratosis according to an embodiment of the present invention, for example, safe treatment/prevention with few side effects is possible.

In the present specification, hereinafter, 5-methyl-2-(1-piperazinyl)benzenesulfonic acid is referred to as MPBS. The MPBS is not limited in its form and may include anhydride of MPBS (also referred to as MPBS anhydride), salt of MPBS (also referred to as MPBS salt), hydrate of MPBS or hydrate of the MPBS salt (each also referred to as MPBS hydrate), and solvate of MPBS or solvate of the MPBS salt (each also referred to as MPBS solvate), which are collectively referred to as the MPBS compound of the present invention. The MPBS compound included in a pharmaceutical composition according to an embodiment of the present invention may be, for example, the MPBS anhydride, the MPBS salt, the MPBS hydrate, or the MPBS solvate, and may include only one type thereof or two or more types thereof. A pharmaceutical composition according to an embodiment of the present invention preferably contains the MPBS compound as an active ingredient.

The type of the MPBS salt is not particularly limited, and examples thereof include alkali metal salt, alkaline earth metal salt, amphoteric element salt, amine salt, inorganic acid salt, or organic acid salt. Examples of the alkali metal salt include sodium salt and potassium salt; examples of the alkaline earth metal salt include magnesium salt and calcium salt; and examples of the amphoteric element salt include aluminum salt. Examples of the amine salt include lower alkylamine salt such as triethylamine salt; hydroxy lower alkylamine salt such as 2-hydroxyethylamine salt, bis-(2-hydroxyethyl)amine salt, tris(hydroxymethyl)aminomethane salt, or N-methyl-D-glucamine salt; cycloalkylamine salt such as dicyclohexylamine salt; benzylamine salt such as N,N-dibenzylethylenediamine salt; or dibenzylamine salt. Examples of the inorganic acid salt include hydrochloride, hydrobromide, sulfate, or phosphate, and examples of the organic acid salt include fumarate, succinate, oxalate, or lactate.

The type of the MPBS hydrate is not particularly limited, and an example thereof is monohydrate. Further, the type of the MPBS solvate is not particularly limited. A solvent capable of forming the MPBS solvate is not particularly limited, and is, for example, a non-aqueous solvent, and specific examples thereof include alcohols such as methanol, ethanol, or isopropyl alcohol, acetone, ethyl acetate, methylene chloride, or the like.

In a pharmaceutical composition for keratosis according to an embodiment of the present invention, the MPBS compound is preferably the MPBS anhydride or the MPBS hydrate, more preferably the MPBS hydrate, and specifically, the 5-methyl-2-(1-piperazinyl)benzenesulfonic acid monohydrate (also referred to as MPBS monohydrate).

The MPBS compound is a known compound. The MPBS compound can be synthesized, for example, using the methods described in Japanese Patent Application Laid-Open Publication No. H3-7263, Japanese Patent Application Laid-Open Publication No. H9-221479, European Patent Application Publication No. 390654, European Patent Application Publication No. 779283, U.S. Pat. Nos. 5,053,409, and 5,990,113, and is a compound that can be easily obtained by a person skilled in the art.

The MPBS compound can be substituted with a compound represented by the following general formula (I) described in International Publication WO 03/011296, or a salt thereof, or a hydrate or solvate of any of these.

Chemical Formula 1

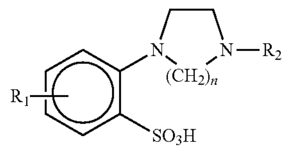

(I)

wherein $R_1$ represents a hydrogen atom, a $C_1$-$C_6$ alkyl group, a $C_3$-$C_7$ cycloalkyl group, a $C_1$-$C_4$ halogenated alkyl group, a halogen atom, or a $C_6$-$C_{12}$ aryl group; $R_2$ represents a hydrogen atom, a $C_1$-$C_6$ alkyl group, or a $C_7$-$C_{12}$ aralkyl group, the aralkyl group may have one or more substituents selected from a group of a cyano group, a nitro group, a $C_1$-$C_6$ alkoxy group, a halogen atom, a $C_1$-$C_6$ alkyl group, and an amino group; and n represents an integer from 1 to 4.

In the general formula (I), examples of the $C_1$-$C_6$ alkyl group defined by $R_1$ include methyl, ethyl, propyl, isopropyl, butyl, isobutyl, sec-butyl, tert-butyl, pentyl, isopentyl, neopentyl, tert-pentyl, hexyl, and isohexyl groups. Examples of the $C_3$-$C_7$ cycloalkyl group include cyclopropyl, cyclobutyl, cyclopentyl, cyclohexyl, and cycloheptyl groups. Examples of the $C_1$-$C_4$ halogenated alkyl group include trifluoromethyl, trifluoroethyl, and pentafluoroethyl groups. Examples of the halogen atom include fluorine, chlorine, and bromine atoms. Examples of the $C_6$-$C_{12}$ aryl group include phenyl and naphthyl groups.

Preferred examples of $R_1$ include, for example, a hydrogen atom, a $C_1$-$C_6$ alkyl group, a $C_5$-$C_6$ cycloalkyl group, a trifluoromethyl group, a halogen atom, or a phenyl group; more preferred examples include, for example, a $C_1$-$C_3$ alkyl group, a cyclohexyl group, a trifluoromethyl group, a chlorine atom, a bromine atom, or a phenyl group; and even more preferred examples include a methyl group or a propyl group, with a methyl group being particularly preferred.

Examples of a $C_1$-$C_6$ alkyl group defined by $R_2$ include the alkyl group defined by $R_1$ above. Examples of a $C_7$-$C_{12}$ aralkyl group include a benzyl group, a phenethyl group, and a naphthylmethyl group. This aralkyl group may have, for example, one or more substituents selected from a group of a $C_1$-$C_6$ alkoxy group such as a cyano group, a nitro group, a methoxy group, an ethoxy group, a propoxy group, an isopropoxy group, a butoxy group, an isobutoxy group, a tert-butoxy group, a pentyloxy group, an isopentyloxy group, a tert-pentyloxy group, or a hexyloxy group; a halogen atom as defined by $R_1$ above; an alkyl group as defined by $R_1$ above; and an amino group.

Preferred examples of $R_2$ include, for example, a hydrogen atom, a $C_1$-$C_3$ alkyl group, and a $C_7$-$C_{12}$ aralkyl group, where the aralkyl group may have one or more substituents selected from a $C_1$-$C_3$ alkyl group, a $C_1$-$C_3$ alkoxy group, and a halogen atom, and more preferred examples include a hydrogen atom and a $C_7$-$C_{12}$ aralkyl group, where the aralkyl group may have one or more substituents selected from a $C_1$-$C_3$ alkoxy group, with a hydrogen atom being particularly preferred. Further, in the above general formula (I), n is preferably 2.

In a pharmaceutical composition for keratosis according to an embodiment of the present invention, the MPBS compound may be, for example, in an ionized form. When a pharmaceutical composition for keratosis according to an embodiment of the present invention is, for example, a liquid as will be described later, and contains an aqueous solvent, a non-aqueous solvent, or a mixed solvent thereof, the MPBS compound may be ionized regardless of whether it is in the form of an anhydride, a salt, a hydrate, or a solvate. The molecular form of the 5-methyl-2-(1-piperazinyl)benzenesulfonic acid (MPBS) is, for example, represented by the following formula (II) and can become an ionized molecular species in a protic solvent such as water. Specifically, examples of the molecular species include a monovalent cation of the following formula (IIIa), a zwitterion having both positive and negative charges of the following formula (IIIb), or a monovalent anion of the following formula (IIIc). The monovalent cation molecular species can, for example, form a salt with an acid (anion), and the monovalent anion can, for example, form a salt with a base (cation).

A pharmaceutical composition for keratosis according to an embodiment of the present invention can be used, for example, for treatment or prevention of keratosis, and the treatment and prevention are, for example, as described above. A pharmaceutical composition for keratosis according to an embodiment of the present invention can be interpreted as, for example, a pharmaceutical composition used for symptoms of keratosis, and specifically, as a pharmaceutical composition used for treatment or prevention of symptoms of keratosis. Further, the treatment or prevention of keratosis can also be referred to as, for example, suppression of keratosis.

The keratosis targeted by the present invention is a disease that causes hyperkeratosis. Hyperkeratosis refers to keratin proliferation in the epidermis of the skin. The keratosis is, for example, a disease caused by an abnormal differentiation process of keratinocytes. An embodiment of the present invention is preferably applied to keratosis involving, for example, IL-22 signaling among keratoses. The IL-22 signaling refers to, for example, a signal generated by an action of IL-22 on an IL-22 receptor.

The keratosis targeted by the present invention is not particularly limited, and examples thereof include Darier's disease, psoriasis, and actinic keratosis.

Examples of psoriasis include psoriasis vulgaris, psoriatic arthritis, guttate psoriasis, erythrodermic psoriasis, pustular psoriasis, and palmoplantar pustulosis.

A pharmaceutical composition for keratosis according to an embodiment of the present invention can, for example, suppress pathological symptoms of the keratosis. The pathological symptoms to be suppressed include, for example, at least one selected from a group of hyperkeratosis, dyskeratosis, and acantholysis, with hyperkeratosis being preferably included. That is, a pharmaceutical composition for keratosis according to an embodiment of the present invention may suppress, for example, hyperkeratosis, dyskeratosis, or acantholysis, and may suppress any one of these symptoms, two or more of the symptoms, or all of the symptoms. According to a pharmaceutical composition for keratosis according to an embodiment of the present invention, it is possible to, for Chemical Formula 2

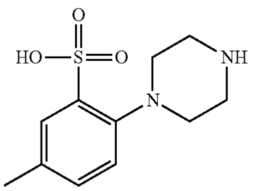

(II)

Molecular type

Chemical Formula 3

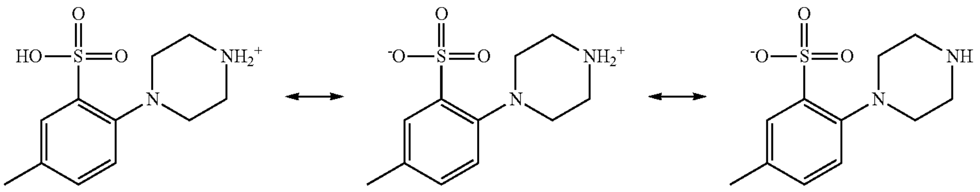

(IIIa) (IIIb) (IIIc)

example, suppress hyperkeratosis; suppress both hyperkeratosis and dyskeratosis; suppress both hyperkeratosis and acantholysis; or suppress hyperkeratosis, dyskeratosis, and acantholysis.

Hyperkeratosis is, for example, keratin proliferation caused by abnormalities in keratinization in the stratum corneum, granular layer, and spinous layer of the skin, and can be observed as thickening of the stratum corneum. Examples of hyperkeratosis include hyperkeratosis involving IL-22 signaling. Dyskeratosis refers to, for example, a process in the spinous layer of the skin where keratinocytes individually keratinize to become abnormal keratinocytes, and in the case of Darier's disease, can be observed as corresponds. Acantholysis is, for example, a state in the spinous layer of the skin where keratinocytes have lost cell adhesion, and can be observed as, for example, clefts or blister formation within the epidermis. Hyperkeratosis, dyskeratosis, and acantholysis can be observed, for example, by collecting lesional skin from a patient and examining it according to methods known to a person skilled in the art.

When the keratosis is Darier's disease, as pathological symptoms, for example, hyperkeratosis in the stratum corneum, granular layer, and spinous layer, dyskeratosis in the spinous layer, and acantholysis in the spinous layer are observed. According to a pharmaceutical composition for keratosis according to an embodiment of the present invention, for example, these pathological symptoms can be simultaneously suppressed. Further, when the keratosis is psoriasis, as a pathological symptom, hyperkeratosis in the stratum corneum, granular layer, and spinous layer is observed. According to a pharmaceutical composition for keratosis according to an embodiment of the present invention, for example, hyperkeratosis in these layers can be suppressed. Further, when the keratosis is actinic keratosis, as pathological symptoms, atypia in the basal layer and/or spinous layer is observed, and hyperkeratosis and dyskeratosis in the epidermis are observed. According to a pharmaceutical composition for keratosis according to an embodiment of the present invention, for example, these symptoms in the epidermis can be suppressed.

According to a pharmaceutical composition for keratosis according to an embodiment of the present invention, for example, the patient's IGA (Investigator's Global Assessment) score can be improved. Here, the IGA score is not particularly limited. The IGA score is generally classified into multiple stages, with higher scores indicating more severe symptoms.

A pharmaceutical composition for keratosis according to an embodiment of the present invention can, for example, suppress or improve clinical symptoms of the body caused by the keratosis, and specifically, can, for example, suppress or improve at least one selected from a group of lesional skin area, pruritus (itching), pain, and odor in the keratosis. According to the pharmaceutical composition for keratosis, for example, by suppressing or improving the above-described pathological symptoms, the clinical symptoms of the body exemplified here can consequently be suppressed or improved.

The lesional skin area is, for example, an area where keratinized papules are observed. A pharmaceutical composition for keratosis according to an embodiment of the present invention can suppress or improve the lesional skin area to, for example, 90% or less, 80% or less, 70% or less, 60% or less, 50% or less, 40% or less, 30% or less, 20% or less, or 10% or less, compared to before administration.

Pruritus can be evaluated, for example, by assessing pruritus felt by a subject using a numerical rating scale for pruritus or a similar method. In the numerical rating scale, for example, 0 indicates no pruritus and 10 indicates the worst pruritus the subject can imagine, and the subject evaluates pruritus using this scale. A pharmaceutical composition for keratosis according to an embodiment of the present invention can reduce a post-administration value on the numerical rating scale for pruritus by, for example, 1 or more, 2 or more, 3 or more, 4 or more, 5 or more, 6 or more, 7 or more, 8 or more, or 9 or more, compared to a pre-administration value.

Pain can be evaluated, for example, by assessing the pain felt by a subject using a numerical rating scale for pain or a similar method. In the numerical rating scale, for example, 0 indicates no skin pain and 10 indicates the worst skin pain the subject can imagine, and the subject evaluates skin pain using this scale. A pharmaceutical composition for keratosis according to an embodiment of the present invention can reduce a post-administration value on the numerical rating scale for pain by, for example, 1 or more, 2 or more, 3 or more, 4 or more, 5 or more, 6 or more, 7 or more, 8 or more, or 9 or more, compared to a pre-administration value.

Odor can be evaluated, for example, by assessing the odor perceived by a subject using a numerical rating scale for odor or a similar method. In the numerical rating scale, for example, 0 indicates no odor and 10 indicates the worst odor the subject can imagine, and the subject evaluates odor using this scale. A pharmaceutical composition for keratosis according to an embodiment of the present invention can reduce a post-administration value on the numerical rating scale for odor by, for example, 1 or more, 2 or more, 3 or more, 4 or more, 5 or more, 6 or more, 7 or more, 8 or more, or 9 or more, compared to a pre-administration value.

A pharmaceutical composition for keratosis according to an embodiment of the present invention improves at least one selected from a group of PGIS (Patient Global Impression of Severity), PGIC (Patient Global Impression of Change), CGIS (Clinician Global Impression of Severity), CGIC (Clinician Global Impression of Change), DLQI (Dermatology Life Quality Index), and Skindex-29 in the keratosis.

(1) PGIS is a single questionnaire that evaluates a subject's overall impression of severity with a score. A pharmaceutical composition for keratosis according to an embodiment of the present invention can improve PGIS and improve the score.

(2) PGIC is a single questionnaire that evaluates a subject's overall degree of improvement in health condition with a score. A pharmaceutical composition for keratosis according to an embodiment of the present invention can improve PGIC and improve the score.

(3) CGIS is a single questionnaire that evaluates a physician's overall impression of a subject's severity with a score. A pharmaceutical composition for keratosis according to an embodiment of the present invention can improve CGIS and improve the score.

(4) CGIC is a single questionnaire that evaluates a degree of improvement in a subject's overall health condition by a physician with a score. A pharmaceutical composition for keratosis according to an embodiment of the present invention can improve CGIC and improve the score.

(5) DLQI is a questionnaire that evaluates each question regarding a subject's QOL with a score. A pharmaceutical composition for keratosis according to an embodiment of the present invention can improve DLQI and improve the score.

(6) Skindex-29 is a questionnaire that evaluates each question regarding a subject's QOL with a score. A pharmaceutical composition for keratosis according to an embodiment of the present invention can improve Skindex-29 and improve the score.

An administration method of a pharmaceutical composition for keratosis according to an embodiment of the present invention is not particularly limited, and may be oral administration or parenteral administration. Examples of parenteral administration include transdermal, subcutaneous, intravenous, intraarterial, intraperitoneal, intranasal, and enteral administration.

A dosage form of a pharmaceutical composition for keratosis according to an embodiment of the present invention is not particularly limited, and can be appropriately determined, for example, depending on the administration method. The dosage form is, for example, liquid, gel, cream, or solid. Examples of oral dosage forms include granules, fine granules, powders, tablets, capsules (for example, hard capsules and soft capsules), syrups, emulsions, suspensions, liquids, and jellies. Further, examples of parenteral dosage forms include injections, suppositories, transdermal agents, and the like.

A pharmaceutical composition for keratosis according to an embodiment of the present invention contains the MPBS compound, and other compositions are not particularly limited. A pharmaceutical composition for keratosis according to an embodiment of the present invention may, for example, contain only the MPBS compound as an active ingredient, or may further contain other active ingredients for keratosis in addition to the MPBS compound.

A pharmaceutical composition for keratosis according to an embodiment of the present invention may, for example, contain only the active ingredient, or may further contain an additive in addition to the active ingredient. The additive is preferably, for example, a pharmaceutically acceptable substance. The type of the additive is not particularly limited, and can be appropriately selected, for example, depending on the dosage form. Examples of the additive include carriers, excipients, stabilizers, lubricants, sweeteners, preservatives, suspending agents, dispersants, thickeners, pH adjusters, antifoaming agents, and flavoring agents. Examples of the carriers include liquids, solids, gels, and creams.

A subject of administration of a pharmaceutical composition for keratosis according to an embodiment of the present invention is not particularly limited, and may be, for example, a human or a non-human animal, with a human being preferred. A non-human animal is, for example, a non-human mammal such as a mouse, a rat, a rabbit, or a horse.

Administration conditions of a pharmaceutical composition for keratosis according to an embodiment of the present invention are not particularly limited, and can be appropriately determined, for example, depending on the administration method and patient information. The patient information may include, for example, age, sex, body weight, the presence or absence of keratosis and its symptoms, the severity of keratosis and its symptoms, and medical history.

When a pharmaceutical composition for keratosis according to an embodiment of the present invention is administered orally, the following conditions can be exemplified. The following examples can be appropriately adjusted for infants, toddlers, children, adults, or elderly patients according to their patient information and the like. A dose of the MPBS compound can be expressed, for example, as a dose calculated as the MPBS anhydride. The doses exemplified below are doses of the MPBS compound calculated as the MPBS anhydride, and as a specific example, are doses of the MPBS monohydrate calculated as the MPBS anhydride.

Daily Dose of the MPBS Compound (Amount Calculated as the MPBS Anhydride)

Lower limit: For example, 1 mg, 10 mg, 20 mg, 25 mg, 30 mg, 50 mg, 60 mg, 100 mg, 150 mg, 200 mg, or 300 mg Upper limit: For example, 300 mg, 400 mg, 500 mg, 600 mg, 800 mg, 1000 mg, or 1200 mg Range: For example, 1-1000 mg, 10-1000 mg, 20-1000 mg, 25-1000 mg, 30-1000 mg, 50-1000 mg, 60-1000 mg, 100-1000 mg, 1-600 mg, 10-600 mg, 25-600 mg, 30-600 mg, 50-600 mg, 100-600 mg, 10-500 mg, 20-500 mg, 25-500 mg, 30-500 mg, 50-500 mg, 60-500 mg, 100-500 mg, 200-500 mg, 10-400 mg, 20-400 mg, 25-400 mg, 30-400 mg, 50-400 mg, 60-400 mg, 100-400 mg, 200-400 mg, 10-300 mg, 20-300 mg, 25-300 mg, 30-300 mg, 50-300 mg, 60-300 mg, 100-300 mg, 200-300 mg, 10-200 mg, 20-200 mg, 25-200 mg, 30-200 mg, 50-200 mg, 60-200 mg, 100-200 mg, 10-100 mg, 20-100 mg, 25-100 mg, 30-100 mg, 50-100 mg, 60-100 mg, 300-400 mg, 300-500 mg, 300-600 mg, 300-800 mg, 300-1000 mg, 300-1200 mg, 400-600 mg, 400-800 mg, 400-1000 mg, 400-1200 mg, 500-600 mg, 500-800 mg, 500-1000 mg, 500-1200 mg, 600-800 mg, 600-1000 mg, or 600-1200 mg.

Specific examples of the dose: For example, 1 mg, 10 mg, 20 mg, 25 mg, 30 mg, 40 mg, 50 mg, 100 mg, 150 mg, 200 mg, 250 mg, 300 mg, 350 mg, 400 mg, 450 mg, 500 mg, 550 mg, 600 mg, 700 mg, 800 mg, 900 mg, 1000 mg, or 1200 mg.

Number of administrations per day: For example, 1 to 3 times; preferably 1 or 2 times; and more preferably 2 times.

Frequency (interval) of administration: For example, daily.

When a pharmaceutical composition for keratosis according to an embodiment of the present invention is administered orally, administration timing can be freely set, for example, before a meal, during a meal, immediately after a meal, after a meal, between meals, when waking up, or when going to bed, with administration between meals being desirable. The inter-meal administration of a pharmaceutical composition for keratosis according to an embodiment of the present invention refers to, for example, regarding a time interval from intake of a meal to administration, administration at least 1 hour after, preferably at least 2 hours after intake of a meal, and/or, for example, regarding a time interval from administration to the next meal, the next meal is taken at least 1 hour after, 2 hours after, 3 hours after, 4 hours after, or 4.5 hours after administration, preferably 1 hour after administration. That is, a pharmaceutical composition for keratosis according to an embodiment of the present invention is administered, for example, between 1 hour or 2 hours after a meal and 1 hour, 2 hours, 3 hours, 4 hours, or 4.5 hours before the next meal.

As described above, a pharmaceutical composition for keratosis according to an embodiment of the present invention can be used for treating or preventing symptoms of keratosis, and as described above, keratosis is a disease that causes hyperkeratosis. Therefore, an embodiment of the present invention can also be referred to as, for example, a pharmaceutical composition for hyperkeratosis that treats or prevents hyperkeratosis. Further, an embodiment of the present invention can also be referred to as, for example, a pharmaceutical composition for hyperkeratosis and acantholysis that simultaneously treats or prevents hyperkeratosis and acantholysis. Further, an embodiment of the present invention can also be referred to as, for example, a pharmaceutical composition for hyperkeratosis, acantholysis, and dyskeratosis that simultaneously treats or prevents hyperkeratosis, acantholysis, and dyskeratosis.

Method for Treating or Preventing Keratosis

A method for treating or preventing keratosis according to an embodiment of the present invention includes a process of administering 5-methyl-2-(1-piperazinyl)benzenesulfonic acid to a subject. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. Unless otherwise specified, a method for treating or preventing keratosis according to an embodiment of the present invention is hereinafter referred to as a treatment/prevention method for keratosis according to an embodiment of the present invention. A treatment/prevention method according to an embodiment of the present invention is characterized by administering the MPBS compound, and other conditions and processes are not particularly limited.

In the treatment/prevention method, the subject is a patient, and the patient may be, for example, a patient who has developed keratosis or a patient who has not developed keratosis.

In the treatment/prevention method, the administration of the MPBS compound is, for example, administration of a pharmaceutical composition for keratosis according to an embodiment of the present invention. In an embodiment of the present invention, the MPBS compound, its composition, its administration method, and the like can incorporate the descriptions regarding a pharmaceutical composition for keratosis according to an embodiment of the present invention.

Use of the MPBS Compound

An embodiment of the present invention is 5-methyl-2-(1-piperazinyl)benzenesulfonic acid for use in treating or preventing keratosis. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. In an embodiment of the present invention, the MPBS compound, its composition, its method of use, and the like can incorporate the descriptions regarding a pharmaceutical composition for keratosis according to an embodiment of the present invention.

Further, an embodiment of the present invention is a use of 5-methyl-2-(1-piperazinyl)benzenesulfonic acid in manufacturing a pharmaceutical composition for keratosis. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. In an embodiment of the present invention, the MPBS compound, its composition, its method of use, and the like can incorporate the descriptions regarding a pharmaceutical composition for keratosis according to an embodiment of the present invention.

Pharmaceutical Composition for Acantholysis and Its Use

A pharmaceutical composition for acantholysis according to an embodiment of the present invention is characterized by containing 5-methyl-2-(1-piperazinyl)benzenesulfonic acid. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. A pharmaceutical composition for acantholysis according to an embodiment of the present invention may contain, for example, only one type of the MPBS compound, or may contain two or more types of the MPBS compound. The MPBS compound can be used for treating or preventing acantholysis. A pharmaceutical composition for acantholysis according to an embodiment of the present invention is characterized by containing the MPBS compound, and other compositions and conditions are not particularly limited. A pharmaceutical composition for acantholysis according to an embodiment of the present invention preferably contains the MPBS compound as an active ingredient. When a pharmaceutical composition for acantholysis according to an embodiment of the present invention is used for treating or preventing acantholysis, the type of disease causing acantholysis as a pathological symptom is not particularly limited.

According to the pharmaceutical composition for acantholysis described above, treatment or prevention of acantholysis can be performed. A pharmaceutical composition for acantholysis according to an embodiment of the present invention may be used, for example, for the purpose of treatment, for the purpose of prevention, or for the purpose of both treatment and prevention. Hereinafter, in the present specification, the term "treatment/prevention" can be interpreted as meaning treatment, prevention, or both treatment and prevention. According to a pharmaceutical composition for acantholysis according to an embodiment of the present invention, for example, safe treatment/prevention with few side effects is possible. Examples of diseases in which acantholysis occurs include Darier's disease, actinic keratosis, Grover's disease, acantholytic blistering, transient acantholytic dermatosis, pemphigus, keratoacanthoma, squamous cell carcinoma, chickenpox, shingles, and herpes simplex.

In the pharmaceutical composition for acantholysis, the MPBS compound, its composition, and its method of use are not particularly limited, and can, for example, incorporate the descriptions regarding a pharmaceutical composition for keratosis according to an embodiment of the present invention described above. Upon incorporation, "keratosis" and "symptoms of keratosis" can be read as "acantholysis."

A method for treating or preventing acantholysis according to an embodiment of the present invention includes a process of administering 5-methyl-2-(1-piperazinyl)benzenesulfonic acid to a subject. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. Unless otherwise specified, a method for treating or preventing acantholysis according to an embodiment of the present invention is hereinafter referred to as a treatment/prevention method for acantholysis according to an embodiment of the present invention. A treatment/prevention method according to an embodiment of the present invention is characterized by ministering the MPBS compound, and other conditions and processes are not particularly limited. A subject as a target of the present invention is, for example, a patient who has developed or may develop acantholysis as a pathological symptom, and the type of disease that causes acantholysis as a pathological symptom is not particularly limited.

In an embodiment of the present invention, the MPBS compound, its composition, its administration method, and the like are not particularly limited, and can incorporate the descriptions regarding a pharmaceutical composition for keratosis according to an embodiment of the present invention. Upon incorporation, "keratosis" and "symptoms of keratosis" can be read as "acantholysis."

In an embodiment of the present invention is 5-methyl-2-(1-piperazinyl)benzenesulfonic acid for use in treating or preventing antholysis. As described above, the form of 5-methyl-2-(1-piperazinyl)benzenesulfonic acid (MPBS) is not limited and may be any type of the MPBS compound, that is, the MPBS anhydride, the MPBS salt, the MPBS hydrate, and/or the MPBS solvate. In an embodiment of the present invention, the MPBS compound, its composition, and its method of use can incorporate the descriptions regarding a pharmaceutical composition for keratosis according to an embodiment of the present invention. Upon incorporation, "keratosis" and "symptoms of keratosis" can be read as "acantholysis."

Further, an embodiment of the present invention is a use of 5-methyl-2-(1-piperazinyl)benzenesulfonic acid in manufacturing a pharmaceutical composition for antholysis. As described above, the form of 5-methyl-2-(1-piperazinyl) benzenesulfonic acid (MPBS) is not limited and may be any type of the MPBS compound, that is, the MPBS anhydride, the MPBS salt, the MPBS hydrate, and/or the MPBS solvate. In an embodiment of the present invention, the MPBS compound, its composition, and its method of use can incorporate the descriptions regarding a pharmaceutical composition for keratosis according to an embodiment of the present invention. Upon incorporation, "keratosis" and "symptoms of keratosis" can be read as "acantholysis."

EXAMPLES

In the following examples, 5-methyl-2-(1-piperazinyl) benzenesulfonic acid monohydrate (hereinafter may be referred to as Compound A in the examples) was used as the MPBS compound.

Example 1 Suppression of Epidermal Thickening in an In Vitro Hyperkeratosis Model A suppressive effect of Compound A on epidermal thickening was evaluated using an epidermal hyperkeratosis model.

When IL-22 is brought into contact with epidermal tissue, thickening is induced in the spinous layer, and hyperkeratosis occurs. Therefore, in the present example, Compound A was added concurrently with IL-22 to an in vitro constructed epidermal tissue to confirm the suppressive effect of Compound A on hyperkeratosis.

Test Cells and Test Design

An IL-22-induced human keratinocyte epidermal hyperkeratosis model was prepared using the following method. As cells, human primary keratinocytes (foreskin, Lonza, 00192906) pooled from three lots of White newborn donors were used. Epilife culture medium (Thermo Fisher Scientific, M-EPI-500-A) was used to culture the human primary keratinocytes. The human primary keratinocytes were subjected to three-dimensional culture using inserts for air-liquid interface culture and a 24-well plate (starting on Day 0), and an in vitro epidermal tissue was prepared over 14 days of culture (Day 0 to Day 14). Culture environment conditions were maintained at 37° C. and 5% $CO_2$. After 14 days (Day 14) since the start (Day 0) of the three-dimensional culture, an aqueous solution of Compound A (solvent: water) and an IL-22 solution (solvent: phosphate-buffered saline, hereinafter may be referred to as PBS) were added to the culture medium of the in vitro epidermal tissue, and the three-dimensional culture was continued for an additional 3 days (Day 14 to Day 17). In the culture medium, final concentration of Compound A was set to 0, 1, 3, 10, or 30 μmol/L, and final concentration of IL-22 was set to 0 or 20 ng/mL. During the three-dimensional culture, the culture medium was basically replaced daily from Day 0 to Day 13 (not replaced on weekend, Saturday and Sunday), and from Day 14 to Day 17, the culture medium was replaced daily, and on each replacement, additions of the Compound A aqueous solution and the IL-22 solution were similarly performed. After 17 days (Day 17) since the start of the three-dimensional culture, the in vitro epidermal tissue was sampled and used for evaluation. In the present specification, the term "final concentration" regarding solutions of test substances, reagents, and the like refers to the concentration in the culture medium at the final stage after all test substances, reagents, and the like have been added.

Each model group of the in vitro epidermal tissue was prepared by combining the concentrations of Compound A and IL-22 in the culture medium as shown in the table below.

TABLE 1

| | | Epidermal hyperkeratosis model | | | | |
|---|---|---|---|---|---|---|
| | Normal group | Control group | Example group | | | |
| | 1-N | 1-C | 1-1 | 1-2 | 1-3 | 1-4 |
| IL-22 (ng/mL) | 0 | 20 | 20 | 20 | 20 | 20 |
| Compound A (μmol/L) | 0 | 0 | 1 | 3 | 10 | 30 |

Evaluation Method

The sampled in vitro epidermal tissue was fixed in a 4% formaldehyde solution, dehydrated, and embedded in paraffin. From the paraffin-embedded tissue, 6 μm thick sections were prepared using a slicer (Leica microtome RM2245), fixed onto glass slides, and used as epidermal tissue slides.

The epidermal tissue slides were stained with hematoxylin and eosin (HE staining) as samples for pathological evaluation. For pathological analysis, three images were captured for each stained sample using an optical microscope (Nikon Eclipse (Ni-E)) connected to a digital camera (DS-Ri2). By image analysis using NIS-Elements AR software (Nikon), epidermal thickness was measured in three images for each sample, and an average value was taken as a representative value for that sample. Hyperkeratosis caused by IL-22 is a factor in spinous layer thickening. In three-dimensional culture, although hyperkeratosis of the stratum corneum occurs, it peels off each time, making quantitative evaluation difficult. Therefore, epidermal thickness measurements were conducted excluding the stratum corneum. The number of samples was set at 3 to 9 epidermal tissue slides per experiment (per group). Then, results of four example groups (1-1, 1-2, 1-3, and 1-4) and a control group (1-C) from Table 1 were integrated and analyzed to evaluate the effect of Compound A. With an average value of a normal group (1-N) (without IL-22 addition) set as 100%, relative values (%) for the measured values of each group, along with their average values and standard deviations, were calculated.

Statistical Analysis

Statistical analysis was performed using MATLAB (registered trademark), with the significance level set at two-sided 5%. The pharmacological effect of Compound A was determined by a pairwise comparison between the control group (1-C) (IL-22 added; Compound A not added) and each example group (IL-22 added; Compound A added), and Aspin-Welch t-test was used as the test method. P-values were adjusted for multiple comparisons using the Bonferroni method.

These results are shown in FIG. 1. FIG. 1 is a graph showing epidermal thickness in the in vitro epidermal tissue. In FIG. 1, the vertical axis represents the thickness of reconstituted human epidermis, expressed as a relative value (%) with the normal group (1-N) (IL-22 not added) set as 100%. As shown in FIG. 1, compared to the normal group (1-N) (IL-22 not added), the control group (1-C) (IL-22 added) exhibited a significant increase in epidermal thickness. In contrast, in the example groups (IL-22 added; Compound A added), the epidermal thickness decreased in a concentration-dependent manner compared to the control group (1-C). These results demonstrate that Compound A can suppress IL-22-induced hyperkeratosis in the epidermis in a concentration-dependent manner at least at concentrations of 1 μmol/L or higher. Further, the hyperkeratosis suppression effect of Compound A was statistically significant at concentrations of 10 μmol/L or higher.

Example 2 Suppression of Acantholysis and Dyskeratosis in an In Vitro Epidermal Acantholysis Model A suppressive effect of Compound A on acantholysis and dyskeratosis were evaluated using an epidermal acantholysis model. In the present example, acantholysis was evaluated using intercellular adhesion strength as an indicator and was pathologically evaluated, and dyskeratosis was evaluated using frequency of pyknotic nuclei appearance as an indicator and was pathologically evaluated.

Test Cells and Test Design

A human keratinocyte epidermal acantholysis model was prepared using the following method. As cells, human primary keratinocytes (foreskin, Lonza, 00192906) pooled from three lots of White newborn donors were used. EpiLife (trademark) culture medium (Thermo Fisher Scientific, M-EPI-500-A) was used to culture the human primary keratinocytes. Thapsigargin was used to induce acantholysis and dyskeratosis.

The human primary keratinocytes were subjected to three-dimensional culture using inserts for air-liquid interface culture and a 24-well plate (starting on Day 0), and an in vitro epidermal tissue was prepared over 14 days of culture. Culture environment conditions were maintained at 37° C. and 5% $CO_2$. After 14 days (Day 14) since the start (Day 0) of the three-dimensional culture, an aqueous solution of Compound A (solvent: water) and a thapsigargin solution (solvent: DMSO) were added to the culture medium of the in vitro epidermal tissue, and the three-dimensional culture was continued for an additional 3 days (Day 14 to Day 17). In the culture medium, final concentration of Compound A was set to 0, 1, 3, 10, or 30 μmol/L, and final concentration of thapsigargin was set to 0 or 30 nmol/L. During the three-dimensional culture, the culture medium was basically replaced daily from Day 0 to Day 17 (not replaced on weekend, Saturday and Sunday), and from Day 14 to Day 17, the culture medium was replaced daily, and on each replacement, additions of the Compound A aqueous solution and the thapsigargin solution were similarly performed. After 17 days (Day 17) since the start of the three-dimensional culture, the in vitro epidermal tissue was sampled and used for evaluation.

Each model group of the in vitro epidermal tissue was prepared by combining the concentrations of Compound A and thapsigargin in the culture medium as shown in the table below.

TABLE 2

| | | Epidermal acantholysis model | | | |
|---|---|---|---|---|---|
| | Normal group | Control group | Example group | | |
| | 2-N | 2-C | 2-1 | 2-2 | 2-3 |
| Thapsigargin (nmol/L) | 0 | 30 | 30 | 30 | 30 |
| Compound A (μmol/L) | 0 | 0 | 1 | 3 | 10 |

Evaluation Method

As described below, acantholysis was evaluated by cell adhesion strength based on biotin diffusion, acantholysis score assessment based on pathological observation, and immunofluorescence staining of cell adhesion marker proteins. Dyskeratosis was evaluated by frequency of pyknotic nuclei appearance based on pathological observation and immunofluorescence staining of keratinocyte differentiation marker proteins. Specifically, the in vitro epidermal tissue sampled from the same well of the 24-well plate was used to prepare slides and perform evaluation.

(1) Biotin Diffusion

The sampled in vitro epidermal tissue was rinsed twice with PBS/$CaCl_2$) (1 mmol/L) solution (hereinafter the same), and then, a biotin marker (EZ-link (trademark) Sulfo-NHS-LC-Biotin, Thermo Fisher Scientific) was added to the epidermal tissue as a cell membrane-impermeable marker molecule. In the present example, in particular, to confirm cell adhesion in the spinous layer of the epidermal tissue, the biotin marker was added to the basal layer side of the epidermal tissue. The biotin marker was suspended in PBS at a concentration of 2 mg/mL, and this suspension was added to the basal layer side. Then, the in vitro epidermal tissue was incubated at 37° C. for 30 minutes and then rinsed twice with a PBS/$CaCl_2$) (1 mmol/L)/Glycine (100 mmol/L) solution (hereinafter the same). Here, to blind the subsequent procedures, sample numbers were coded. Then, the in vitro epidermal tissue was fixed in a 4% formaldehyde solution, dehydrated, and embedded in paraffin. From the paraffin-embedded tissue, 6 μm thick sections were prepared using a slicer (Leica microtome RM2245), fixed onto glass slides, and used as epidermal tissue slides.

When acantholysis occurs, the amount of biotin in the epidermal layer relatively increases due to a decrease in cell adhesion strength. Therefore, using the prepared epidermal tissue slides, the intercellular adhesion strength in the epidermis of the in vitro epidermal tissue was evaluated by detecting the biotin marker. That is, the epidermal tissue slides were first deparaffinized, rehydrated, and then incubated in the presence of fluorescently labeled streptavidin (Thermo Fisher Scientific, S32354) to detect biotin (the molecular marker) that had diffused into the epidermal layer of the in vitro epidermal tissue.

Specifically, in a dark environment at 4° C., three images were captured for each sample (the epidermal tissue slides) using an optical microscope (Nikon Eclipse (Ni-E)) connected to a digital camera (DS-Ri2). Image analysis was performed using NIS-Elements AR software (Nikon) to quantify the biotin fluorescence intensity in three images per sample. For each image, the epidermal tissue excluding the stratum corneum was manually delineated as a region of interest (ROI), and its surface area (A) (unit: μm2) was measured. Next, an area (B) (unit: μm2) of a biotin-stained region in the delineated region of interest (ROI) was measured. The biotin fluorescence intensity was quantified as a value obtained by multiplying an average staining intensity (C) of the biotin-stained region by the biotin-stained area (B) and dividing by the ROI surface area (A), that is, a staining intensity per unit surface area. For each sample, an average biotin fluorescence intensity was calculated from the three images, and this average value was used as a representative value for the three images. The number of samples was set at 9 epidermal tissue slides per experiment (per in vitro epidermal tissue). Then, with a measured value of a normal group (2-N) (without thapsigargin addition) set as 100%, relative values (%) for the measured values of each group, along with their average values and standard deviations, were calculated.

(2) Pathological Evaluation

The sampled in vitro epidermal tissue was rinsed twice with the PBS/$CaCl_2$) solution, fixed in a 4% formaldehyde solution, dehydrated, and embedded in paraffin. From the paraffin-embedded tissue, 6 μm thick sections were prepared using a slicer (Leica microtome RM2245), fixed onto glass slides, and used as epidermal tissue slides.

The epidermal tissue slides were stained with HE and used as samples for pathological evaluation. For pathological analysis, images were captured for each stained sample using an optical microscope (Nikon Eclipse (Ni-E)) connected to a digital camera (DS-Ri2). Through image analysis of the captured images, dyskeratosis and acantholysis were observationally evaluated for each sample.

When dyskeratosis occurs, the frequency of pyknotic nuclei appearance relatively increases. Therefore, for the pathological evaluation of dyskeratosis, the samples for pathological evaluation were used, and the number of pyknotic nuclei in the field of view was counted. The counting of pyknotic nuclei was performed in three fields of view (three images) per sample, and an average value was taken as a representative value for that sample. The number of samples was set at 9 epidermal tissue slides per experiment (per group). Further, for the pathological evaluation of acantholysis, the samples for pathological evaluation were used, observations were made, and the presence or absence of acantholysis findings was qualitatively recorded. Qualitative assessment of acantholysis findings was performed by scoring the number of clefts observed at the boundary between the basal layer and the spinous layer. Scoring criteria were as follows, and average values and standard deviations of the score values were calculated for each group.

0: No clefts
1: One cleft
2: Two clefts
3: Three or more clefts (3) Immunofluorescence Staining Immunofluorescence staining was performed on the epidermal tissue slides using antibodies corresponding to each target marker.

(i) Similar to (2) above, sections were fixed onto slides to prepare epidermal tissue slides. The epidermal tissue slides were deparaffinized and rehydrated, and then heated with 0.01 mol/L sodium citrate buffer (pH 6.0) to activate antigens. The epidermal tissue slides with activated antigens were rinsed with PBS, and then saturated for 1 hour with a PBS/0.1% Tween20 solution containing 5% normal goat serum (NGS) in a constant temperature and humidity chamber to avoid nonspecific labeling. The epidermal tissue slides were incubated overnight at 4° C. in a constant temperature and humidity chamber with primary antibodies (anti-filaggrin (FLG) antibody and anti-cytokeratin 10 (K-10) antibody). The epidermal tissue slides were sequentially washed with a PBS/0.1% Tween20 solution and PBS, and then incubated for 1 hour at room temperature in a constant temperature and humidity chamber with anti-mouse and anti-rabbit secondary antibodies conjugated with Alexa Fluor dyes. Finally, the epidermal tissue slides were rinsed with PBS. Primary and secondary antibodies used for co-immunostaining of FLG and K-10, which are keratinocyte differentiation-related proteins, are shown in the table below.

TABLE 3

| Primary Antibody | | | Secondary Antibody | | |
|---|---|---|---|---|---|
| Product name | Distributor | Product number | Product name | Distributor | Product number |
| Anti-FLG antibody | Santa Cruz | sc66192 | Anti-mouse Ab 488 | Thermo Fisher Scientific | A11029 |
| Anti-K-10 antibody | Abcam | ab76318 | Anti-rabbit Ab 568 | Thermo Fisher Scientific | A11011 |

(ii) Similar to (i) above, the epidermal tissue slides were deparaffinized and rehydrated, and then heated at 56° C. for 15 minutes with a pepsin solution (Sigma, R2283) to activate antigens. The epidermal tissue slides with activated antigens were rinsed with PBS, and then saturated for 1 hour with a PBS/0.1% Tween20 solution containing 2% bovine serum albumin (BSA) in a constant temperature and humidity chamber to avoid nonspecific labeling. The epidermal tissue slides were incubated overnight at 4° C. in a constant temperature and humidity chamber with primary antibodies (anti-desmoglein 1 (DSG1) antibody and anti-claudin 1 (CLDN1) antibody). The epidermal tissue slides were sequentially washed with a PBS/0.1% Tween20 solution and PBS, and then incubated for 1 hour at room temperature in a constant temperature and humidity chamber with anti-goat and anti-rabbit secondary antibodies conjugated with Alexa Fluor dyes. Finally, the epidermal tissue slides were rinsed with PBS. Primary and secondary antibodies used for co-immunostaining of DSG1/CLDN1, which are cell adhesion-related proteins, are shown in the table below.

TABLE 4

| Primary Antibody | | | Secondary Antibody | | |
|---|---|---|---|---|---|
| Product name | Distributor | Product number | Product name | Distributor | Product number |
| Anti-DSG1 antibody | Thermo Fisher Scientific | PA5-142500 | Anti-goat Ab 488 | Thermo Fisher Scientific | A11055 |
| Anti-CLDN1 antibody | Abcam | ab15098 | Anti-rabbit Ab 568 | Thermo Fisher Scientific | A11011 |

Keratinocyte nuclei can be detected using DAPI (4',6-diamidino-2-phenylindole), a fluorescent molecule that binds to adenine and thymine bases of DNA. Therefore, the epidermal tissue slides from (i) and (ii) above, after the secondary antibody treatment and final washing, were treated with ProLong (trademark)Diamond Antifade Mountant (Thermo Fisher Scientific, P36962) containing DAPI, and immunofluorescence-stained images were obtained.

Specifically, in a dark environment at 4° C., three images were captured for each sample (the epidermal tissue slides) using an optical microscope (Nikon Eclipse (Ni-E)) connected to a digital camera (DS-Ri2). Image analysis was performed using NIS-Elements Advanced Research Imaging software (Nikon) to quantify the fluorescence-stained area in three images per sample. For each image, for FLG, the epidermal tissue including the stratum corneum was manually delineated as a region of interest (ROI), while for K-10, DSG1, and CLDN1, the epidermal tissue excluding the stratum corneum was manually delineated as a region of interest (ROI), and their surface areas (A) (unit: μm2) were measured. Next, an area (B) (unit: μm2) of a stained region within the delineated region of interest (ROI) was measured. An immunostained area was quantified as a value (B/A) obtained by dividing the stained area (B) by the ROI surface area (A), that is, a relative value (%) of the stained area, and the average value and standard deviation were calculated for each group. For each sample, an average biotin fluorescence intensity was calculated from the three images, and this average value was used as a representative value for the three images. The number of samples was set at 9 epidermal tissue slides per experiment (per in vitro epidermal tissue).

Statistical Analysis

Statistical analysis was performed using SAS, with the significance level for the Williams multiple comparison test set at one-sided 2.5% and the significance level for other test methods set at two-sided 5%. The success of forming the epidermal acantholysis model by thapsigargin addition was determined by a two-group comparison between the normal group (2-N) (thapsigargin not add; Compound A not added) and a control group (2-C) (thapsigargin added; Compound A not added), using Student's t-test as the test method. Here, for in vitro epidermal tissues in which no significant change was observed, it was determined that the formation of the epidermal acantholysis model had failed, and no further analysis was performed. Further, the pharmacological effect of Compound A was determined by a comparison between the control group (2-C) (thapsigargin added; Compound A not added) and each example group (thapsigargin added; Compound A added), using the Williams multiple comparison test as the test method. In the evaluation of immunofluorescence staining, only the example group (2-3) (Compound A at 10 μmol/L) was used, so Student's t-test was used as the test method.

Figure 2:
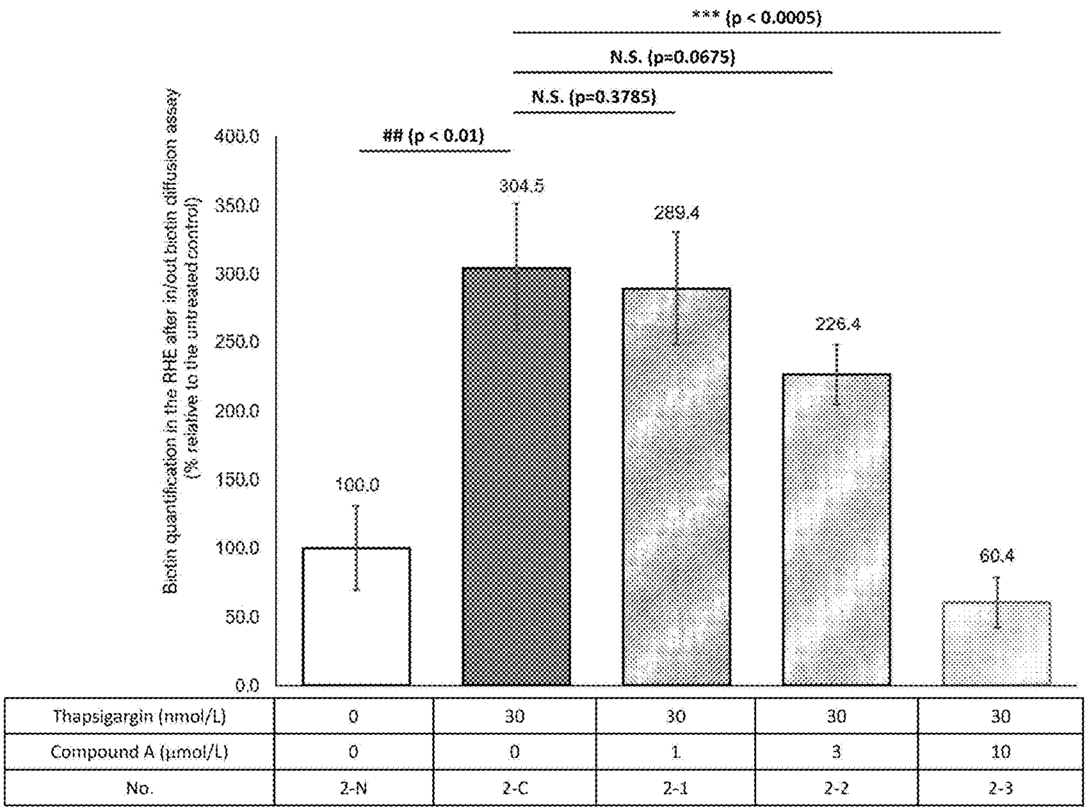
FIG. 2 is a graph showing a relationship between administration of 5-methyl-2-(1-piperazinyl)benzenesulfonic acid monohydrate and biotin diffusion, which is an indicator of acantholysis, in Example 2.
Figure 3:
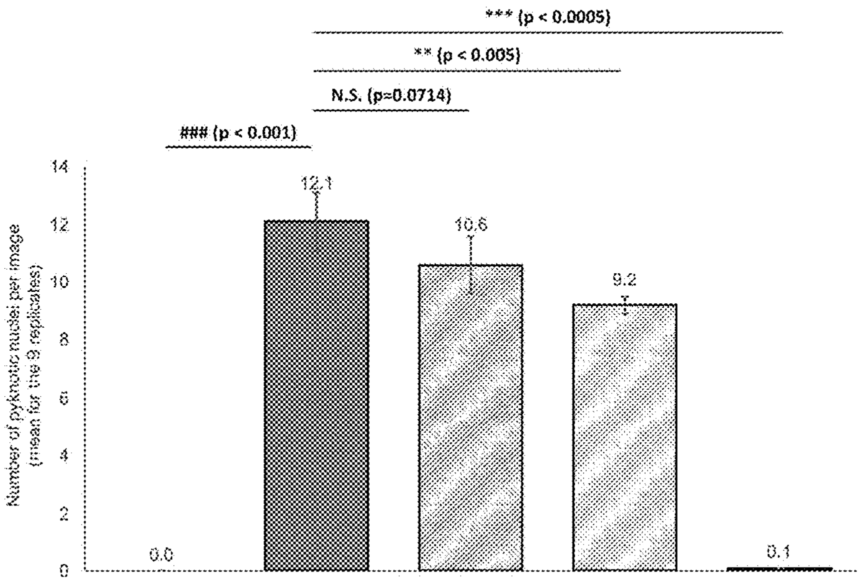
FIG. 3 is a graph showing a relationship between administration of 5-methyl-2-(1-piperazinyl)benzenesulfonic acid monohydrate and pyknotic nuclei frequency, which is an indicator of dyskeratosis, in Example 2.
Figure 4:
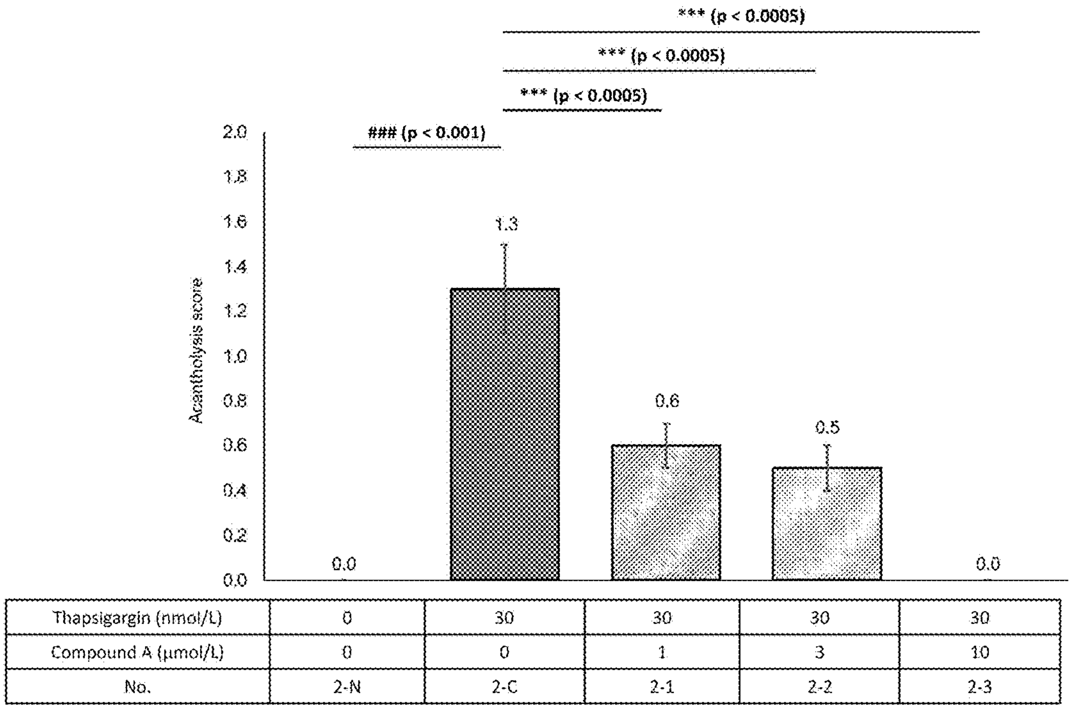
FIG. 4 is a graph showing a relationship between administration of 5-methyl-2-(1-piperazinyl)benzenesulfonic acid monohydrate and pathological evaluation of acantholysis in Example 2.
Figure 5A:
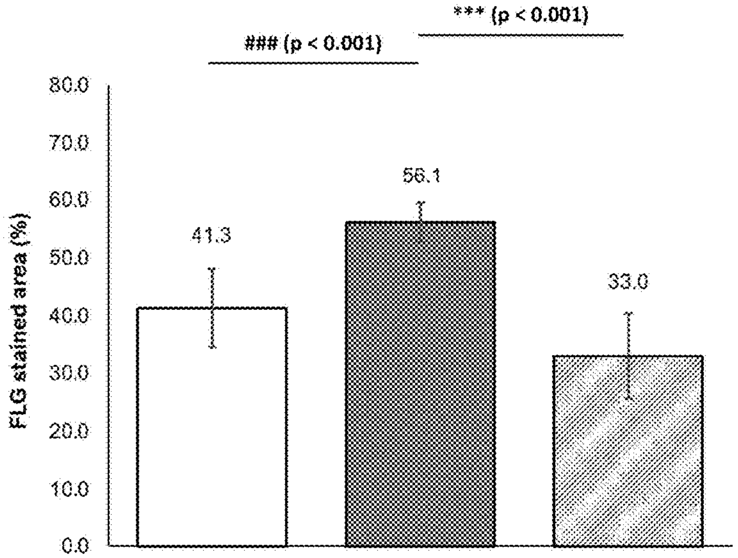
FIG. 5A is a graph showing a relationship between administration of 5-methyl-2-(1-piperazinyl)benzenesulfonic acid monohydrate and expression of keratinocyte differentiation marker molecules associated with dyskeratosis in Example 2.
Figure 5B:
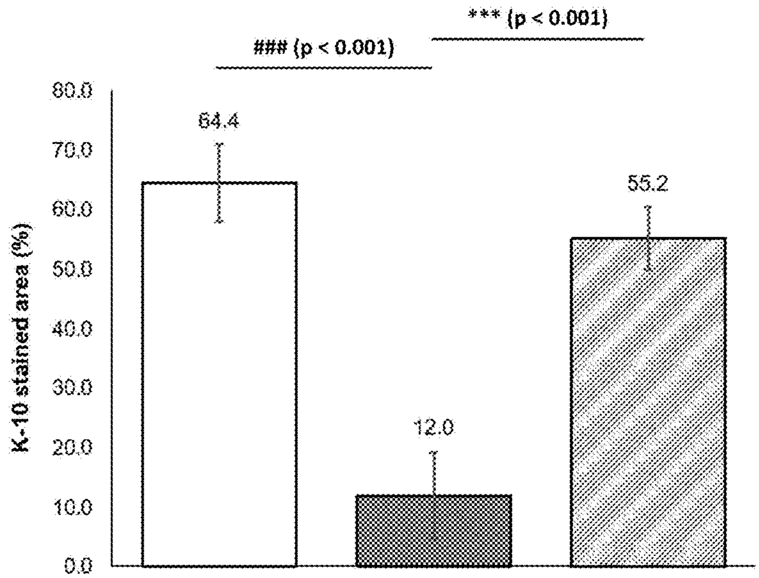
FIG. 5B is a graph showing a relationship between administration of 5-methyl-2-(1-piperazinyl)benzenesulfonic acid monohydrate and expression of keratinocyte differentiation marker molecules associated with dyskeratosis in Example 2.
Figure 6A:
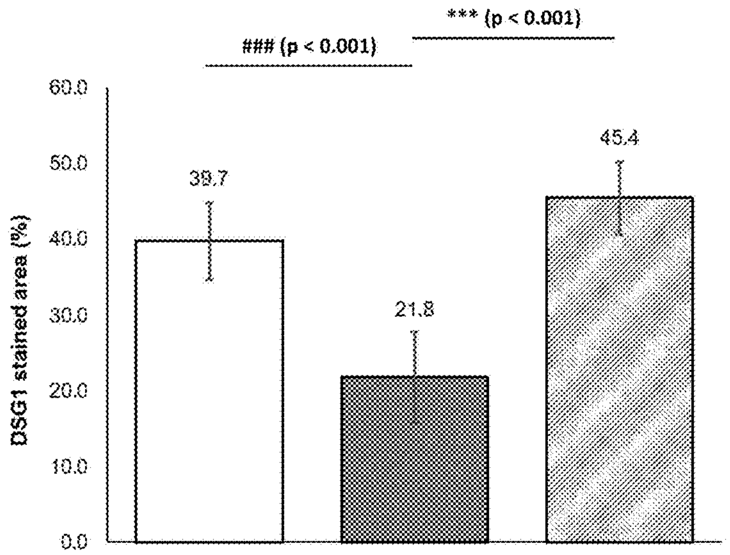
FIG. 6A is a graph showing a relationship between administration of 5-methyl-2-(1-piperazinyl)benzenesulfonic acid monohydrate and expression of cell adhesion marker molecules associated with acantholysis in Example 2.
Figure 6B:
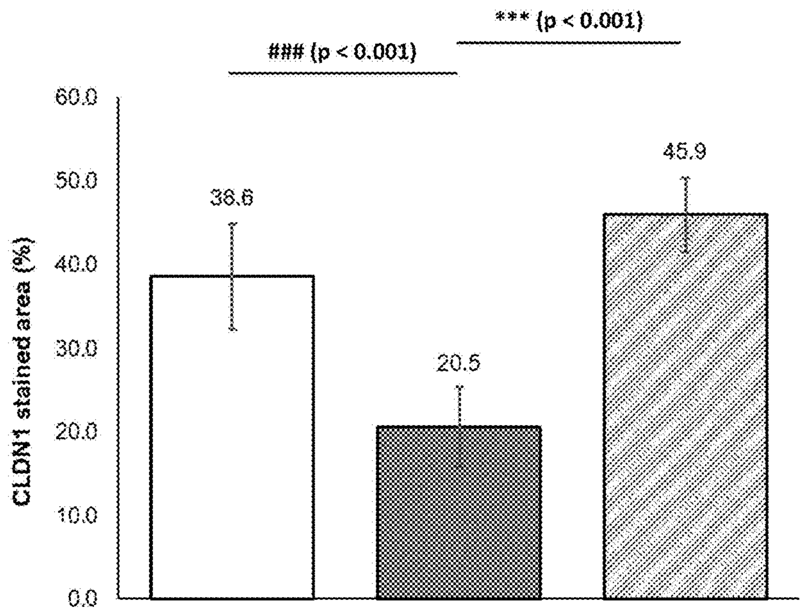
FIG. 6B is a graph showing a relationship between administration of 5-methyl-2-(1-piperazinyl)benzenesulfonic acid monohydrate and expression of cell adhesion marker molecules associated with acantholysis in Example 2.

These results are shown in FIGS. 2, 3, 4, 5A, 5B, 6A, and 6B. FIG. 2 is a graph showing the results of biotin diffusion, which is an indicator of acantholysis, with the vertical axis representing the relative value (%) of the amount of biotin. FIG. 3 is a graph showing the results of pyknotic nuclei frequency, which is an indicator of abnormal keratinosis, with the vertical axis representing the number of pyknotic nuclei in the images. FIG. 4 is a graph showing the results of pathological evaluation of acantholysis, with the vertical axis representing the acantholysis score. FIGS. 5A and 5B are graphs showing the results of keratinocyte differentiation markers related to abnormal keratinosis, with FIG. 5A showing the results for FLG and FIG. 5B showing the results for K-10, each with the vertical axis representing the relative value (%) of the stained area. FIGS. 6A and 6B are graphs showing the results of cell adhesion markers related to acantholysis, with FIG. 6A showing the results for DSG1 and FIG. 6B showing the results for CLDN1, each with the vertical axis representing the relative value (%) of the stained area.

First, acantholysis is described. As shown in FIG. 2, the amount of biotin in the epidermal layer, which is an indicator of acantholysis, significantly increased in the control group (2-C) (thapsigargin added) compared to the normal group (2-N) (thapsigargin not added). This indicates that the addition of thapsigargin caused acantholysis, and the amount of biotin in the epidermal layer increased due to a decrease in intercellular adhesion strength. In contrast, in the example groups in which Compound A was added together with thapsigargin, the amount of biotin in the epidermal layer decreased in a concentration-dependent manner at least at concentrations of 1 μmol/L or higher compared to the control group (2-C). Furthermore, as shown in FIG. 4, the pathological evaluation also showed similar results. Specifically, compared to the normal group (2-N), the acantholysis score of the control group (2-C) significantly increased due to the addition of thapsigargin. However, in the example groups, the addition of Compound A suppressed the increase in the acantholysis score in a concentration-dependent manner at least at concentrations of 1 μmol/L or higher. Further, as shown in FIGS. 6A and 6B, similar results were observed in the immunofluorescence staining of the cell adhesion-related proteins DSG1 and CLDN1. Compared to the normal group (2-N), the immunofluorescence-stained area in the control group (2-C) decreased due to the addition of thapsigargin. That is, this indicates that the addition of thapsigargin weakened or disrupted desmosomes and tight junctions, which are forms of cell adhesion. In contrast, in the example groups where Compound A was added together with thapsigargin, the immunofluorescence-stained area increased compared to the control group (2-C). That is, this indicates that Compound A was able to normalize the abnormality in cell adhesion induced by thapsigargin.

These results demonstrate that the addition of Compound A can improve the reduction in intercellular adhesion strength induced by thapsigargin in in vitro epidermal tissue in a concentration-dependent manner, that is, can suppress acantholysis. Further, as a specific example, Compound A was found to be statistically significant at concentrations of 10 μmol/L or higher in suppressing the reduction in intercellular adhesion strength and statistically significant at concentrations of 1 μmol/L or higher in suppressing the increase in the pathological evaluation score for acantholysis.

Next, dyskeratosis is described. As shown in FIG. 3, the number of pyknotic nuclei, which is an indicator of dyskeratosis, significantly increased in the control group (2-C) (thapsigargin added) compared to the normal group (2-N) (thapsigargin not added). This means that the addition of thapsigargin caused dyskeratosis and increased the number of pyknotic nuclei. In contrast, in the example groups in which Compound A was added together with thapsigargin, the amount of biotin in the epidermal layer decreased in a concentration-dependent manner at least at Compound A concentrations of 1 μmol/L or higher compared to the control group 2-C. Further, as shown in FIGS. 5A and 5B, in the immunofluorescence staining of the differentiation marker FLG expressed in keratinocytes of the granular layer and stratum corneum, and in the immunofluorescence staining of the differentiation marker K-10 expressed in keratinocytes of the spinous layer and granular layer, the immunofluorescence-stained area in the control group (2-C) statistically significantly increased and decreased, respectively, compared to the normal group (2-N), due to the addition of thapsigargin. That is, this indicates that the addition of thapsigargin caused an uneven differentiation state in the keratinocytes forming the spinous layer, making them prone to dyskeratosis. In contrast, in the example group where Compound A was added at 10 μmol/L together with thapsigargin, the immunofluorescence-stained area for FLG and the immunofluorescence-stained area for K-10 were statistically significantly decreased and increased, respectively, compared to the control group (2-C). That is, this indicates that Compound A was able to normalize the abnormality in keratinocyte differentiation induced by thapsigargin.

These results demonstrate that the addition of Compound A can improve the increase in the frequency of pyknotic nuclei appearance induced by thapsigargin in in vitro epidermal tissue in a concentration-dependent manner, that is dyskeratosis is suppressed. Further, as a specific example, Compound A was found to be statistically significant in suppressing the increase in pyknotic nuclei, which is an indicator of dyskeratosis, at concentrations of 3 μmol/L or higher.

Further, these results demonstrate that Compound A can suppress both dyskeratosis and acantholysis. Therefore, for keratosis, including diseases that cause only one of dyskeratosis and acantholysis, as well as diseases that cause both (for example, Darier's disease), administration of Compound A alone can simultaneously suppress both symptoms. Further, in Example 1 above, a hyperkeratosis model was prepared using the same keratinocytes, and the suppression of hyperkeratosis by Compound A was also confirmed. Therefore, it can be said that Compound A exhibits suppressive effects on all three major pathological symptoms of Darier's disease, namely hyperkeratosis, acantholysis, and dyskeratosis.

Example 3 Suppression of Thickening in an In Vivo Hyperkeratosis Model

A suppressive effect of Compound A on dorsal skin thickening was evaluated using a hyperkeratosis model.

By applying imiquimod to the skin of mice, hyperkeratosis accompanied by an inflammatory response can be induced, and a psoriasis-like dermatitis model mouse with hyperkeratosis (skin thickening) can be obtained. Therefore, in the present example, Compound A was administered to mice concurrently with the application of imiquimod, which induces hyperkeratosis, to confirm the suppressive effect of Compound A on hyperkeratosis.

Test Cells and Test Design

Seven-week-old male BALB/c mice (Japan Charles River) were used. The general condition of the mice was observed for 6 days as a quarantine and acclimation period. After the acclimation period (at 8 weeks of age), the body weight of the mice was measured, and the mice were divided into three groups using stratified randomization to ensure that the average body weight was uniform across the groups. Mice in one of the example groups had their dorsal skin shaved, and three days later, under 2% inhalation anesthesia using isoflurane (Mylan Seiyaku Co., Ltd.) as an anesthetic, 5% imiquimod cream (Mochida Pharmaceutical Co., Ltd.) was applied to the dorsal skin of the mice once daily for a total of four days to induce psoriasis-like dermatitis in the mice. Psoriasis-like dermatitis causes hyperkeratosis as a pathological symptom. The amount of 5% imiquimod cream applied per dose was 62.5 mg (equivalent to 3.125 mg of imiquimod). After applying the 5% imiquimod cream, the application site was gently wiped with absorbent cotton soaked in lukewarm water about 4 hours after each application. Concurrently, Compound A was orally administered at a dose of 30 mg (Compound A)/kg, twice daily for 4 days (Day 1 to Day 5), starting on the same day as the application of the 5% imiquimod cream. The twice-daily administration was performed with the first dose given before the application of the 5% imiquimod cream and the second dose given at least 10 hours after the first dose on that day. For the oral administration of Compound A, a 3 mg/mL solution of Compound A (solvent: water for injection) was used.

The remaining two groups were designated as a normal group and a control group. The normal group (3-N) had their dorsal skin shaved but did not undergo imiquimod-induced dermatitis or receive administration of Compound A. The control group (3-C) underwent imiquimod-induced dermatitis in the same manner as the example group above but did not receive administration of Compound A; instead, a 1% Tween80 solution (not containing Compound A) was orally administered at 10 mL/kg.

TABLE 5

| | | Hyperkeratosis model | |
|---|---|---|---|
| | Normal group 3-N | Control group 3-C | Example group 3-1 |
| Imiquimod 5% cream (mg/day) | 0 | 62.5 | 62.5 |
| Compound A (mg/kg, b.i.d.) | 0 | 0 | 30 |

Evaluation Method

With the first day of 5% imiquimod cream application designated as Day 1, the dorsal skin thickness of the mice was measured before dissection on Day 5. Specifically, the mice were placed under 2% inhalation anesthesia with isoflurane, and the dorsal skin thickness was measured using a digital caliper (Mitutoyo Corporation). The measurements were recorded to two decimal places, with the unit being mm. The number of animals per group was set at 9 for the control group and the example group, and 4 for the normal group, to evaluate the effect of Compound A. For dorsal skin thickness, the average value and standard deviation were calculated for each group.

Statistical Analysis

Statistical analysis was performed using SAS, and inter-group comparisons were performed with a significance level set at two-sided 5%. The pharmacological effect of Compound A was determined by a comparison between the control group (3-C) (imiquimod applied; Compound A not administered) and the example group above (imiquimod applied; Compound A administered), and Student's t-test was used as the test method.

Figure 7:
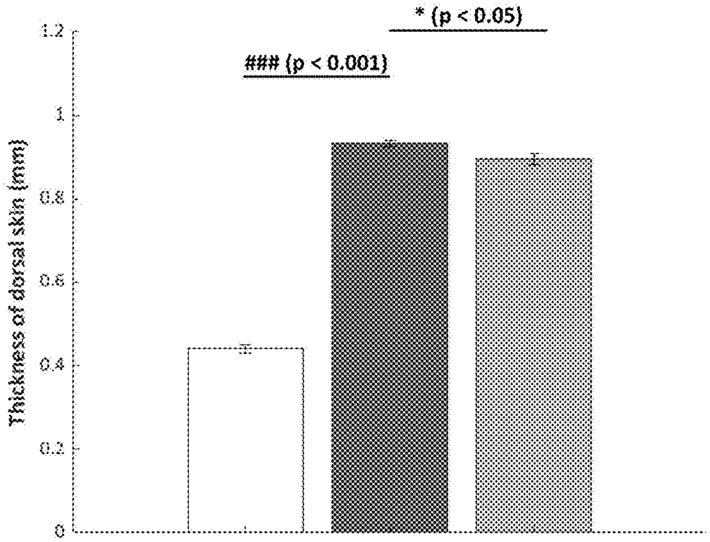
FIG. 7 is a graph showing a relationship between administration of 5-methyl-2-(1-piperazinyl)benzenesulfonic acid monohydrate and dorsal skin thickness in hyperkeratosis mice in Example 3.

These results are shown in FIG. 7. FIG. 7 is a graph showing the dorsal skin thickness on Day 5 in the hyperkeratosis mouse model, with the vertical axis representing the dorsal skin thickness (mm). As shown in FIG. 7, compared to the normal group (3-N), which did not have psoriasis-like dermatitis induced, the control group (3-C), in which psoriasis-like dermatitis was induced with imiquimod, exhibited significant thickening of the dorsal skin, that is, hyperkeratosis. In contrast, in the example group (3-1), where Compound A was administered on the same day as imiquimod application, the dorsal skin thickness was statistically significantly reduced compared to the control group (3-C). These results demonstrate that Compound A can suppress skin thickening, that is, hyperkeratosis, induced by imiquimod.

Example 4 Involvement of IL-22 in Darier's Disease

Gene expression analysis was performed on human formalin-fixed paraffin-embedded (FFPE) skin samples derived from patients with Darier's disease and patients with psoriasis vulgaris. Specifically, the involvement of IL-22 in Darier's disease, a type of keratosis, was evaluated by comparing it with psoriasis vulgaris, another type of keratosis known to involve IL-22.

Test Cells and Test Design

As described below, image acquisition and library preparation were performed using FFPE block samples with diagnostic history (Aurus Bioscience Co., Ltd.). For the patient-derived FFPE block samples, a chest skin biopsy sample from a Black female in her 70s diagnosed with psoriasis vulgaris, and a dorsal skin biopsy sample from a White female in her 40s diagnosed with Darier's disease, were used. From the FFPE block samples, 5 μm thick sections were cut using a slicer, and a section adhesion test was conducted using Visium Test Slides (10× Genomics). After confirming minimal peeling or curling of the sections through the adhesion test, slides were prepared using a commercially available kit (Visium Spatial for FFPE Gene Expression Kit, Human Transcriptome, 10× Genomics). After HE staining the slides, digital slide data were obtained using a scanner (NanoZoomer, Hamamatsu Photonics K.K.). Furthermore, libraries were prepared from the slides using a commercially available kit (Visium Spatial for FFPE Gene Expression Starter Kit, Human Transcriptome, 10× Genomics). Then, next-generation sequencing analysis was performed on the prepared libraries.

Data Analysis and Evaluation Method

Spatial transcriptome analysis of the sequencing data was performed using Space Ranger (10× Genomics). Gene expression intensity was calculated by log 2-transforming UMI counts normalized by the total UMI count of the same barcode sequence. To estimate the contribution of IL-22 to the pathology, the gene expression intensity of IL22RA1, the receptor for IL-22, in the epidermis of Darier's disease patients was compared with that in psoriasis vulgaris, where IL-22 has been reported to significantly contribute to the progression of hyperkeratosis. As keratosis progresses, the number of spots classified as epidermis in Visium increases, forming layers. Therefore, the epidermis was classified into the upper layer and the basal layer, and the expression intensity of IL22RA1 was calculated for each layer of the epidermis. Then, a ratio of IL22RA1 expression in the upper layer to that in the basal layer, where IL22RA1 expression is lower, was calculated.

The results are shown in Table 6. As shown by the IL22RA1 epidermal expression ratio in Table 6, Darier's disease patients exhibited strong gene expression of IL22RA1 (IL-22 receptor) in the upper layer of the epidermis compared to the basal layer, similar to patients with psoriasis vulgaris, where IL-22 involvement is known. This indicates that, similar to psoriasis vulgaris, IL-22 is also involved in Darier's disease.

TABLE 6

| | IL22RA1 expression intensity (log2 mean of normalized UMI count) | | IL22RA1 epidermal expression ratio ((upper |
|---|---|---|---|
| Patient's disease | Epidermis (Upper layer) | Epidermis (Basal layer) | layer)/(basal layer)) |
| Psoriasis vulgaris | 0.60 | 0.26 | 2.31 |
| Darier's disease | 1.14 | 0.30 | 3.80 |

From the above results, the involvement of IL-22 was confirmed in both psoriasis vulgaris and Darier's disease, which are major types of keratosis. In Example 1 above, hyperkeratosis was induced by IL-22, and the suppression of hyperkeratosis by Compound A was confirmed. This indicates that the suppressive effect of Compound A on hyperkeratosis observed in Example 1 can be said to be effective also for both psoriasis vulgaris and Darier's disease.

Example 5 Evaluation of Pharmacokinetics

The pharmacokinetics of Compound A were evaluated. In the present example, the amount of Compound A used is expressed in terms of the amount of the MPBS anhydride (hereinafter may be referred to as Compound B in the examples).

A Phase 1, double-blind, placebo-controlled, dose-escalating repeated oral administration study was conducted in healthy male and female subjects. In this study, Compound A was orally administered once or twice daily to the subjects for evaluation. The single dose of Compound A was set at 50 mg or 100 mg, calculated in terms of the amount of Compound B. A total of 24 subjects (16 males and 8 females) were enrolled in the study, and all 24 completed the study. Table 7 below shows study groups and treatment details. The study consisted of three groups, Groups A to C, as shown in Table 7. Each group consists of 8 subjects, with 6 subjects receiving Compound A and 2 subjects receiving placebo. For the administration of Compound A, tablets containing 5 mg of Compound A calculated in terms of the amount of Compound B (hereinafter referred to as Compound A 5 mg tablets) were used. Groups A and B were administered 10 tablets per dose of either Compound A 5 mg tablets or placebo tablets, while Group C was administered 20 tablets per dose of either Compound A 5 mg tablets or placebo tablets.

TABLE 7

| Study group | Gender | Treatment | Number of subjects |
|---|---|---|---|
| A | Male | Compound A (50 mg as Compound B) or placebo, administered twice daily | 8 |
| B | Female | Compound A (50 mg as Compound B) or placebo, administered twice daily | 8 |
| C | Male | Compound A (100 mg as Compound B) or placebo, administered twice daily | 8 |

Each subject received a total of 16 doses of either Compound A 5 mg tablets or placebo tablets during the study period. The breakdown of the 16 doses was as follows: one dose in the morning on the first day (Day 1), one dose in the morning and one dose in the evening from the third day (Day 3) to the ninth day (Day 9), and one dose in the morning on the tenth day (Day 10). From the third to the tenth days of the study (Day 3 to Day 10), the Compound A 5 mg tablet or placebo tablet was administered at 12-hour intervals. The morning doses were administered about 2 hours after breakfast, and the afternoon doses were administered about 2 hours after dinner. Breakfast, lunch, an afternoon snack, and dinner were provided about 2 hours before, 4 hours after, 7 hours after, and 10 hours after the morning dose, respectively. Meals were controlled to not exceed 2,500 kilocalories for males and 2,000 kilocalories for females. Water intake was prohibited until 2 hours after dosing on Day 1 and Day 10, but otherwise, water could be freely consumed at any time. The study drug (Compound A 5 mg tablets or placebo tablets) was taken with 200 mL of water while standing. On Day 1 and Day 10, subjects were prohibited from assuming a supine position until 2 hours after dosing, except when required by the study protocol or instructed by a physician.

Figure 8:
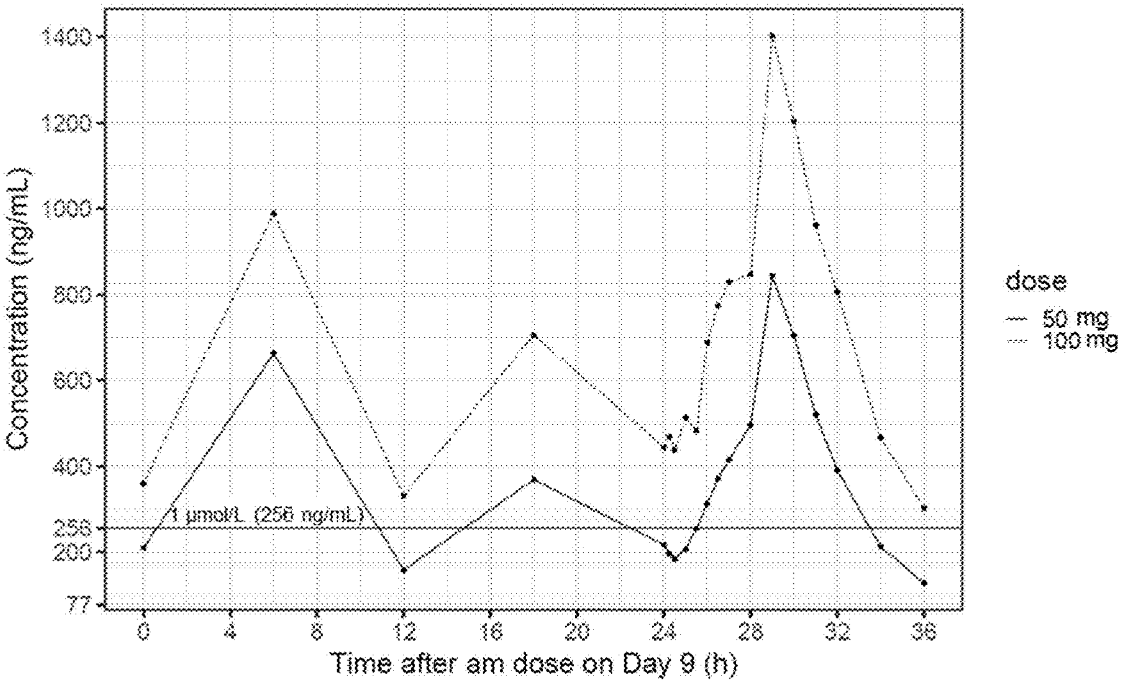
FIG. 8 is a graph showing a relationship between administration of 5-methyl-2-(1-piperazinyl)benzenesulfonic acid monohydrate and average plasma concentration of 5-methyl-2-(1-piperazinyl)benzenesulfonic acid in Example 5.

For Groups A and B (hereinafter referred to as the 50 mg group), which received a single dose of 50 mg of Compound A calculated as the amount of Compound B, and Group C (hereinafter referred to as the 100 mg group), which received a single dose of 100 mg of Compound B, blood samples were collected over time to measure the plasma concentration of Compound B. The average plasma concentration from Day 9 to Day 10 is shown in FIG. 8 and Table 8. FIG. 8 is a graph showing the average plasma concentration of Compound B, with the vertical axis representing the plasma concentration of Compound B (ng/mL) and the horizontal axis representing the elapsed time from dosing on Day 9, with the time immediately before dosing on Day 9 set as 0 hours. The results for the 50 mg group represent the average of 12 subjects from Groups A and B, excluding those who received placebo, and the results for the 100 mg group represent the average of 6 subjects from Group C, excluding those who received placebo.

TABLE 8

| | | Compound B mean plasma concentration (ng/mL) | |
|---|---|---|---|
| Study date | Time point | 50 mg group (N = 12) | 100 mg group (N = 6) |
| Day 9 | Immediately before morning administration | 210.09 | 360.35 |
| Day 9 | 6 hours after administration | 662.47 | 989.32 |
| Day 9 | Immediately before afternoon administration | 158.36 | 331.91 |
| Day 9 | 6 hours after administration | 369.55 | 705.65 |
| Day 10 | Immediately before morning administration | 216.83 | 444.19 |
| Day 10 | 0.25 hours after administration | 196.31 | 469.2 |
| Day 10 | 0.5 hours after administration | 183.86 | 438.34 |
| Day 10 | 1 hour after administration | 206.96 | 513.29 |
| Day 10 | 1.5 hours after administration | 255.71 | 483.13 |
| Day 10 | 2 hours after administration | 313.38 | 687.97 |
| Day 10 | 2.5 hours after administration | 370.99 | 774.88 |
| Day 10 | 3 hours after administration | 416.12 | 828.57 |
| Day 10 | 4 hours after administration | 494.98 | 847.76 |
| Day 10 | 5 hours after administration | 844.08 | 1402.44 |
| Day 10 | 6 hours after administration | 704.55 | 1203.54 |
| Day 10 | 7 hours after administration | 519.75 | 961.36 |
| Day 10 | 8 hours after administration | 392.11 | 805.98 |
| Day 10 | 10 hours after administration | 212.23 | 466.93 |
| Day 10 | 12 hours after administration | 128.57 | 302.48 |

In the results of the thapsigargin-induced human keratinocyte epidermal acantholysis model in Example 2 above, the effective pharmacological concentration of Compound A was about 1 μmol/L (about 256 ng/mL) to about 10 μmol/L (about 2560 ng/ml). Therefore, based on the concentration profile of Compound B in human plasma after administration of Compound A shown in FIG. 8 (drug concentration profile) and the effective pharmacological concentration from Example 2 above, the clinically effective dose of Compound A is, for example, oral administration of about 50 mg or more twice daily in terms of the amount converted to Compound B, and more further, oral administration of 50-200 mg twice daily.

Example 6 In Vivo Clinical Trial

Compound A is administered to patients with Darier's disease to conduct a phase 2 clinical trial. Compound A is administered using Compound A 50 mg tablets containing 50 mg of Compound A calculated in terms of the amount of Compound B.

Subjects

Patients with Darier's disease aged 18 to 75 years.

Study Overview

Randomized, double-blind clinical trial:

Placebo tablet group: 24 subjects 100 mg group: 12 subjects

One Compound A 50 mg tablet was orally administered twice a day (100 mg/day in terms of Compound B)

200 mg group: 24 subjects

Tow Compound A 50 mg tablets were orally administered twice a day (200 mg/day in terms of Compound B)

400 mg group: 24 subjects

Four Compound A 50 mg tablets were orally administered twice a day (400 mg/day in terms of Compound B)

Study Endpoints

In the clinical trial of Compound A in patients with Darier's disease, the following endpoints are evaluated: Investigator's Global Assessment (IGA) score, Body Surface Area (BSA), scores for pruritus, pain, and odor, Patient Global Impression of Severity (PGIS) score, Patient Global Impression of Change (PGIC) score, Clinician Global Impression of Severity (CGIS) score, Clinician Global Impression of Change (CGIC) score, Dermatology Life Quality Index (DLQI) score, Skindex-29 score, and the like. Compared to the placebo tablet group, administration of Compound A is expected to improve at least one or more of the study endpoints.

In Examples 1-4 described above, the suppressive effects on epidermal thickening in epidermal hyperkeratosis, as well as on acantholysis and dyskeratosis in epidermal acantholysis, were confirmed. Therefore, it can be said that various symptom-related scores in patients with Darier's disease are improved by the administration of Compound A.

Example 7 Evaluation of the Effect of Food on Pharmacokinetics

Compound A was administered under fasting conditions or after meals to evaluate the effect of food on pharmacokinetics.

A Phase 1, double-blind, placebo-controlled, four-period crossover study was conducted in healthy male subjects. In this study, subjects were administered a single dose of Compound A in each dosing period (Periods 1 to 4) for evaluation. The single dose of Compound A was set at 25 mg, calculated in terms of Compound B. Nine subjects were enrolled in the study. Table 9 below shows study groups and treatment details. The study consisted of three groups, Groups 1-3, as shown in Table 9. Each group consisted of 3 subjects, with 6 subjects receiving Compound A and 3 subjects receiving placebo in each dosing period. For the administration of Compound A, the Compound A 5 mg tablets from Example 5 above were used.

TABLE 9

Table 9: Study group composition

| | Administration period | | | |
|---|---|---|---|---|
| Study group | 1 | 2 | 3 | 4 |
| 1 | 5 mg (fasted) | 25 mg (fasted) | 25 mg (fed) | Placebo (fasted) |
| 2 | 5 mg (fasted) | Placebo (fasted) | Placebo (fed) | 75 mg (fasted) |
| 3 | Placebo (fasted) | 25 mg (fasted) | 25 mg (fed) | 75 mg (fasted) |

Each subject was orally administered either a Compound A 5 mg tablet or a placebo tablet once in the morning on Day 1 of each dosing period. Food intake was prohibited until 4 hours after dosing, and water intake was prohibited until 2 hours after dosing. The study drug (Compound A 5 mg tablets or placebo tablets) was taken with 240 mL of water while standing. In all dosing periods, dinner was provided on the day before the study (Day 0), and on Day 1, lunch, an afternoon snack, and dinner were provided at 4.5, 7.5, and 11 hours after dosing, respectively. However, in the third dosing period only, a high-fat meal was provided in the morning of Day 1. The high-fat meal was provided 20 minutes before dosing, consumed over 15 minutes, and completed 5 minutes before dosing.

The pharmacokinetic parameters following administration of 25 mg of Compound A under fasting conditions (first, second, and fourth dosing periods) or after a high-fat meal (third administration period) are shown in Table 10. In Table 10, Column A lists the types of parameters; Column B, labeled "25 mg (fed)," shows the average results for the third dosing period; and Column C, labeled "25 mg (fasted)," shows the average results for the second dosing period. In Columns B and C, $T_{max}$ is presented as the median with the minimum and maximum values (in parentheses), while other parameters are presented as the arithmetic average with the standard deviation (in parentheses). In Column D, $T_{max}$ is presented as the least squares average difference with the 95% confidence interval (in parentheses), while other parameters are presented as the least squares average ratio with the 95% confidence interval (in parentheses).

TABLE 10

Mean values (standard deviations) of pharmacokinetic parameters

| | B | C | D Fed/Fasted Least squares mean ratio (95% confidence interval) or |
|---|---|---|---|
| | Administration | | |
| A Parameter | 25 mg (fed) | 25 mg (fasted) | Fed - Fasted Least squares mean difference (95% confidence interval) |
| $AUC_{0-t}$ (ng · h/mL) | 1598 (393) | 2097 (540) | Ratio: 0.77 (0.625, 0.940) |
| $AUC_{0-\infty}$ (ng · h/mL) | 1612 (393) | 2068 (594) | Ratio: 0.73 (0.593, 0.902) |
| $C_{max}$ (ng/mL) | 207 (52.2) | 267 (76.3) | Ratio: 0.79 (0.610, 1.02) |
| $t_{max}$* (h) | 5.00 (3.00, 6.00) | 6.00 (6.00, 6.00) | Difference: −1.50 (−3.00, 0) |
| $t_{1/2\alpha}$ (h) | 2.74 (0.120) | 2.65 (0.228) | |
| $t_{1/2\beta}$ (h) | 10.9 (1.82) | 9.00 (1.82) | |

*Median (min-max)

The high-fat meal intake resulted in decreases of 23%, 27%, and 21% in the area under the drug concentration curve from 0 hours post-dose to the last quantifiable time point ($AUC_{0-t}$), the area under the drug concentration curve from 0 hours post-dose to infinity ($AUC_{0-\infty}$), and maximum plasma concentration ($C_{max}$), respectively. The time to maximum concentration ($T_{max}$) was slightly earlier with the high-fat meal intake compared to fasting administration.

According to a pharmaceutical composition according to an embodiment of the present invention, by containing 5-methyl-2-(1-piperazinyl)benzenesulfonic acid, keratosis can be treated or prevented.

Darier's disease is a type of keratosis, a skin disorder, and is a condition in which keratotic papules appear due to hyperkeratosis, acantholysis, and dyskeratosis in the epidermis. Pain, pruritus (itching), and the like are reported as frequent symptoms, and malodor occurs particularly in flexural areas prone to excessive sweating and secondary infections. Moreover, since Darier's disease is prone to chronicity and recurrence, it is accompanied by a decline in patients' quality of life (hereinafter also referred to as QOL), and social handicap is also a concern.

In particular, among keratoses, Darier's disease currently lacks a fundamental treatment method recommended by guidelines, and treatment is centered on disease management and symptom control by avoiding exacerbating factors. Treatment methods involving the administration of retinoids, steroids, vitamin D analogs, and the like have been proposed, but side effects have also been reported, and no treatment provides safe and consistent effects. Therefore, there remains a significant unmet medical need for safe and effective treatment.

A pharmaceutical composition for keratosis according to an embodiment of the present invention contains 5-methyl-2-(1-piperazinyl)benzenesulfonic acid (also referred to as 5-methyl-2-(piperazin-1-yl)benzenesulfonic acid).

A method for treating or preventing keratosis according to an embodiment of the present invention includes a process of administering 5-methyl-2-(1-piperazinyl)benzenesulfonic acid to a subject.

An embodiment of the present invention is 5-methyl-2-(1-piperazinyl)benzenesulfonic acid for use in treating or preventing keratosis.

An embodiment of The present invention is a use of 5-methyl-2-(1-piperazinyl)benzenesulfonic acid in manufacturing a pharmaceutical composition for keratosis.

According to a pharmaceutical composition according to an embodiment of the present invention, by containing 5-methyl-2-(1-piperazinyl)benzenesulfonic acid, keratosis can be treated or prevented.

A pharmaceutical composition for keratosis according to an embodiment of the present invention includes 5-methyl-2-(1-piperazinyl)benzenesulfonic acid.

In the pharmaceutical composition, the 5-methyl-2-(1-piperazinyl)benzenesulfonic acid may be an anhydrate thereof, a salt thereof, a hydrate or solvate thereof, or a hydrate or solvate of a salt thereof.

In the pharmaceutical composition, the 5-methyl-2-(1-piperazinyl)benzenesulfonic acid may be an anhydrate thereof, a salt thereof, a hydrate thereof, or a hydrate of a salt thereof.

In the pharmaceutical composition, the hydrate may be 5-methyl-2-(1-piperazinyl)benzenesulfonic acid monohydrate.

In the pharmaceutical composition, the keratosis may be at least one selected from a group of Darier's disease, psoriasis, and actinic keratosis.

In the pharmaceutical composition, the keratosis may be Darier's disease or psoriasis.

In the pharmaceutical composition, the keratosis may be Darier's disease.

In the pharmaceutical composition, the keratosis may be psoriasis.

In the pharmaceutical composition, the psoriasis may be psoriasis vulgaris.

In the pharmaceutical composition, the keratosis may be a keratosis in which IL-22 signaling is involved.

The pharmaceutical composition may be for suppressing at least one selected from a group of hyperkeratosis, dyskeratosis, and acantholysis in the keratosis.

In the pharmaceutical composition, the hyperkeratosis may be a hyperkeratosis in which IL-22 signaling is involved.

The pharmaceutical composition may be for improving IGA score in the keratosis.

The pharmaceutical composition may be for suppressing or improving at least one selected from a group of lesional skin area, itching, pain, and odor in the keratosis.

In the pharmaceutical composition, dosage of 5-methyl-2-(1-piperazinyl)benzenesulfonic acid may be 1 to 1000 mg/day. The dosage is an amount calculated as anhydrate of 5-methyl-2-(1-piperazinyl)benzenesulfonic acid.

In the pharmaceutical composition, the dosage may be 50 to 600 mg/day.

In the pharmaceutical composition, the dosage may be 100 to 400 mg/day.

In the pharmaceutical composition, the number of administrations per day may be 1 to 3.

In the pharmaceutical composition, the number of administrations per day may be 2.

In the pharmaceutical composition, administration interval may be daily administration.

A method for treating or preventing keratosis according to an embodiment of the present invention includes a process of administering 5-methyl-2-(1-piperazinyl)benzenesulfonic acid to a subject.

In the method, the 5-methyl-2-(1-piperazinyl)benzenesulfonic acid may be an anhydrate thereof, a salt thereof, a hydrate or solvate thereof, or a hydrate or solvate of a salt thereof.

In the method, the 5-methyl-2-(1-piperazinyl)benzenesulfonic acid may be an anhydrate thereof, a salt thereof, a hydrate thereof, or a hydrate of a salt thereof.

In the method, the hydrate may be 5-methyl-2-(1-piperazinyl)benzenesulfonic acid monohydrate.

In the method, an administration method may be oral administration.

In the method, a dose per day may be 1 to 1000 mg/day. The dose is an amount calculated as anhydrate of 5-methyl-2-(1-piperazinyl)benzenesulfonic acid.

In the method, the number of administrations per day may be 1 to 3.

In the method, administration interval may be daily administration.

5-Methyl-2-(1-piperazinyl)benzenesulfonic acid according to an embodiment of the present invention is for use in treating or preventing keratosis.

In the 5-methyl-2-(1-piperazinyl)benzenesulfonic acid, the 5-methyl-2-(1-piperazinyl)benzenesulfonic acid may be an anhydrate thereof, a salt thereof, a hydrate or solvate thereof, or a hydrate or solvate of a salt thereof.

In the 5-methyl-2-(1-piperazinyl)benzenesulfonic acid according to [29], the 5-methyl-2-(1-piperazinyl)benzenesulfonic acid may be an anhydrate thereof, a salt thereof, a hydrate thereof, or a hydrate of a salt thereof.

In the 5-methyl-2-(1-piperazinyl)benzenesulfonic acid, the hydrate may be 5-methyl-2-(1-piperazinyl)benzenesulfonic acid monohydrate.

Use of 5-methyl-2-(1-piperazinyl)benzenesulfonic acid according to an embodiment of the present invention is in manufacturing a pharmaceutical composition for keratosis.

In the use, the 5-methyl-2-(1-piperazinyl)benzenesulfonic acid may be an anhydrate thereof, a salt thereof, a hydrate or solvate thereof, or a hydrate or solvate of a salt thereof.

In the use, the 5-methyl-2-(1-piperazinyl)benzenesulfonic acid may be an anhydrate thereof, a salt thereof, a hydrate thereof, or a hydrate of a salt thereof.

In the use, the hydrate may be 5-methyl-2-(1-piperazinyl) benzenesulfonic acid monohydrate.

A pharmaceutical composition for acantholysis according to an embodiment of the present invention includes 5-methyl-2-(1-piperazinyl)benzenesulfonic acid.

In the pharmaceutical composition, the 5-methyl-2-(1-piperazinyl)benzenesulfonic acid may be an anhydrate thereof, a salt thereof, a hydrate or solvate thereof, or a hydrate or solvate of a salt thereof.

In the pharmaceutical composition, the 5-methyl-2-(1-piperazinyl)benzenesulfonic acid may be an anhydrate thereof, a salt thereof, a hydrate thereof, or a hydrate of a salt thereof.

In the pharmaceutical composition, the hydrate may be 5-methyl-2-(1-piperazinyl)benzenesulfonic acid monohydrate.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for treating Darier's disease, comprising:
administering an effective amount of a pharmaceutical composition comprising 5-methyl-2-(1-piperazinyl) benzenesulfonic acid to a subject in need thereof.

2. The method of claim 1, wherein the pharmaceutical composition is orally administered to the subject in need thereof.

3. The method of claim 1, wherein the pharmaceutical composition is parenterally administered to the subject in need thereof.

4. The method of claim 1, wherein the pharmaceutical composition is administered to the subject in need thereof such that a dosage of the 5-methyl-2-(1-piperazinyl)benzenesulfonic acid is in a range of 1 to 1000 mg/day.

5. The method of claim 2, wherein the pharmaceutical composition is administered to the subject in need thereof such that a dosage of the 5-methyl-2-(1-piperazinyl)benzenesulfonic acid is in a range of 1 to 1000 mg/day.

6. The method of claim 3, wherein the pharmaceutical composition is administered to the subject in need thereof such that a dosage of the 5-methyl-2-(1-piperazinyl)benzenesulfonic acid is in a range of 1 to 1000 mg/day.

7. The method of claim 1, wherein the pharmaceutical composition is administered to the subject in need thereof such that at least one of hyperkeratosis in a stratum corneum, a granular layer and a spinous layer, dyskeratosis in a spinous layer, and acantholysis in a spinous layer is suppressed.

8. The method of claim 1, wherein the pharmaceutical composition is administered daily to the subject in need thereof.

9. The method of claim 1, wherein the pharmaceutical composition is administered to the subject in need thereof in a range of 1 to 3 times per day.

10. The method of claim 1, wherein the subject in need thereof is a patient in need thereof.

11. The method of claim 4, wherein the pharmaceutical composition is administered to the subject in need thereof such that at least one of hyperkeratosis in a stratum corneum, a granular layer and a spinous layer, dyskeratosis in a spinous layer, and acantholysis in a spinous layer is suppressed.

12. The method of claim 4, wherein the pharmaceutical composition is administered daily to the subject in need thereof.

13. The method of claim 4, wherein the pharmaceutical composition is administered to the subject in need thereof in a range of 1 to 3 times per day.

14. The method of claim 4, wherein the subject in need thereof is a patient in need thereof.

15. The method of claim 1, wherein the pharmaceutical composition is administered to the subject in need thereof such that a dosage of the 5-methyl-2-(1-piperazinyl)benzenesulfonic acid is in a range of 10 to 500 mg/day.

16. The method of claim 1, wherein the pharmaceutical composition is administered to the subject in need thereof such that a dosage of the 5-methyl-2-(1-piperazinyl)benzenesulfonic acid is in a range of 100 to 400 mg/day.

17. The method of claim 2, wherein the pharmaceutical composition is administered to the subject in need thereof such that a dosage of the 5-methyl-2-(1-piperazinyl)benzenesulfonic acid is in a range of 10 to 500 mg/day.

18. The method of claim 2, wherein the pharmaceutical composition is administered to the subject in need thereof such that a dosage of the 5-methyl-2-(1-piperazinyl)benzenesulfonic acid is in a range of 100 to 400 mg/day.

19. The method of claim 10, wherein the pharmaceutical composition is administered to the patient in need thereof such that a dosage of the 5-methyl-2-(1-piperazinyl)benzenesulfonic acid is in a range of 10 to 500 mg/day.

20. The method of claim 10, wherein the pharmaceutical composition is administered to the patient in need thereof such that a dosage of the 5-methyl-2-(1-piperazinyl)benzenesulfonic acid is in a range of 100 to 400 mg/day.

* * * * *